(12) United States Patent
Bracaglia et al.

(10) Patent No.: US 9,795,471 B2
(45) Date of Patent: Oct. 24, 2017

(54) POLYMER-TISSUE HYBRID BIOMATERIALS AND METHODS OF MAKING AND USING SAME

(71) Applicant: University of Maryland, College Park, College Park, MD (US)

(72) Inventors: Laura Bracaglia, Herndon, VA (US); Poonam Sharma, Conshohocken, PA (US); John Patrick Fisher, Kensington, MD (US)

(73) Assignee: University Of Maryland, College Park, College Park, MD (US)

( * ) Notice: Subject to any disclaimer, the term of this patent is extended or adjusted under 35 U.S.C. 154(b) by 205 days.

(21) Appl. No.: 14/869,193

(22) Filed: Sep. 29, 2015

(65) Prior Publication Data

US 2016/0089476 A1   Mar. 31, 2016

Related U.S. Application Data

(60) Provisional application No. 62/056,780, filed on Sep. 29, 2014.

(51) Int. Cl.
| | |
|---|---|
| *A61F 13/00* | (2006.01) |
| *A61F 2/00* | (2006.01) |
| *A61F 13/02* | (2006.01) |
| *A61K 38/18* | (2006.01) |
| *A61F 2/02* | (2006.01) |
| *A61L 27/54* | (2006.01) |
| *A61L 27/56* | (2006.01) |
| *A61L 27/48* | (2006.01) |

(52) U.S. Cl.
CPC ............... *A61F 2/02* (2013.01); *A61L 27/48* (2013.01); *A61L 27/54* (2013.01); *A61L 27/56* (2013.01); *A61F 2210/0004* (2013.01); *A61F 2210/0076* (2013.01); *A61L 2420/02* (2013.01); *A61L 2420/08* (2013.01); *A61L 2430/20* (2013.01)

(58) Field of Classification Search
None
See application file for complete search history.

(56) References Cited

U.S. PATENT DOCUMENTS

| | | |
|---|---|---|
| 6,355,055 B1 | 3/2002 | Waksman et al. |
| 7,833,267 B2 | 11/2010 | Flagle et al. |
| 8,075,615 B2 | 12/2011 | Eberhardt et al. |
| 2013/0150957 A1 | 6/2013 | Weber |
| 2014/0050689 A1 | 2/2014 | Pathak et al. |

FOREIGN PATENT DOCUMENTS

EP          2878315          6/2015

OTHER PUBLICATIONS

Henslee et al.; J. Biomed Mater Res Part A; 2015:103A:1485-1497 (published online Aug. 5, 2014).*

* cited by examiner

*Primary Examiner* — Jeffrey T Palenik
(74) *Attorney, Agent, or Firm* — Hodgson Russ LLP

(57) ABSTRACT

Provided are hybrid biomaterials comprising one or more layers of cross-linked poly(propylene fumarate) and/or cross-linked copolymer comprising a plurality of cross-linked propylene fumarate moieties. The layers may further comprise a plurality of microparticles, a plurality of micropores, or both a plurality of microparticles and a plurality of micropores encapsulated within the cross-linked poly(propylene fumarate) and/or cross-linked copolymer comprising a plurality of cross-linked propylene fumarate moieties. One of the layers is disposed on a compliant matrix dense tissue substrate (e.g., a pericardium tissue substrate). The hybrid biomaterials can be used, for example, in method of repairing tissue defects.

18 Claims, 15 Drawing Sheets

(15 of 15 Drawing Sheet(s) Filed in Color)

POLYMER-TISSUE HYBRID BIOMATERIALS AND METHODS OF MAKING AND USING SAME

CROSS-REFERENCE TO RELATED APPLICATIONS

This application claims priority to U.S. Provisional Application No. 62/056,780, filed on Sep. 29, 2014, the disclosure of which is hereby incorporated herein by reference.

STATEMENT REGARDING FEDERALLY SPONSORED RESEARCH

This invention was made with government support under contract no. R01 AR061460-01A1 awarded by The National Institutes of Health. The government has certain rights in the invention.

BACKGROUND OF THE DISCLOSURE

For more than 50 years, a method to replace malfunctioning or diseased tissue in the cardiovascular system has been an important area of development. Each year, over 275,000 replacement valves and 600,000 vascular grafts are implanted to correct damaged native structures. Complex pediatric and general cardiac surgeries also utilize tissue or synthetic patch material in reconstruction and repair. When considering materials for prosthetic applications, biological tissues offer some clear advantages over synthetic substitutes. Aside from the inherent biocompatibility, biological tissues possess "intelligent" elastic and mechanical properties that are unable to be mimicked by manmade material.

One biological tissue commonly used is pericardium. Pericardial tissue has historically been selected for cardiovascular devices due to its availability, inherent strength, and elastic properties. In addition to the desirable mechanical behavior, natural tissue often demonstrates superior fluid dynamic properties, and when compared to synthetic materials, requires less anticoagulation therapy.

In order to capitalize on and maintain the natural properties of pericardium, previous research has focused on improving the durability and biocompatibility of the material upon implantation. However, and despite significant advances, clinical experience continues to highlight the challenges of the prolonged use of pericardium implants in the cardiovascular system.

All natural tissue, including pericardium, can elicit an inflammatory and immune response from the host. To combat these events, pericardial tissue is commonly preserved in glutaraldehyde (GA), which chemically crosslinks the tissue's collagen molecules. This crosslinking process is effective at stabilizing the tissue against chemical and enzymatic degradation, as well as lessening the display of antigenic determinants. However, the crosslinked product has been associated with local cytotoxicity and, more importantly, severe calcification of the material that can over time lead to subsequent matrix deterioration and compromised mechanical properties.

The detailed pathways controlling calcification of cardiovascular tissue, both natural and prosthetic, are not explicitly understood, but as the most common pathology recorded in heart valve failures, it is certainly a process under high investigation. It is observed that chemically crosslinking pericardium damages and distorts the natural structure, destroys interstitial cells, and diminishes potential for viable cell inhabitation. The specialized matrix consisting of collagen, elastin and glycosaminoglycans that composes pericardium is responsible for allowing the tissue to accommodate the constant changes in shape and stress transfer, and is therefore essential to maintain. Damaging this natural structure and removing native cells results in a tissue that can no longer maintain or repair itself. It has been suggested in literature that calcification and eventual ossification is the result of insufficient or irregular repair of the tissue network. In culture, myofibroblasts have been shown to undergo phenotypic differentiation into the osteoblast like cells seen in calcified cardiac tissue, promoting calcification and bone type remodeling. Others suggest that the origin of bone cells in ossified valves in unknown, but their presence is confirmed in observation of excised heart valves and tissue.

Original damage leading to the irregular repair of the implanted tissue can be a result of mechanical stress, immune cell infiltration, or other pathologies, which complicates the investigation of the process. In one theory, responding immune cells are reported to secrete collagenase, among other proteolytic enzymes, which immediately begin to degrade the collagen network. It is further hypothesized by some that this initial proteolysis of crosslinked collagen debris creates foci for calcium deposition to initialize. Studies have shown a cooperative relationship between calcification of this type of tissue and the inflammatory response, enzymatic degradation, and microstructural failure (both independent failures and those associated with calcium deposits).

Regardless of the mechanism directly controlling the calcium deposits, GA treatment has been shown through both in vivo and in vitro accelerated testing to destroy the surface endothelium of the tissue, autolytically disrupt interstitial cells, alter natural collagen bundles, and destroy native GAGS. Despite the discrepancies in origin of the deterioration, a strong correlation between GA treated tissue and increased calcification suggests that the chemical fixation of the tissue further inhibits the appropriate remodeling.

Previous approaches to mitigate these limitations have focused on lessening the extent of crosslinking and resulting calcification by minimizing crosslinking time and by utilizing washing steps to removed excess GA. Although these successes reduce drawbacks of GA treated pericardium, any crosslinking process alters the natural tertiary structure of proteins that make up the tissue and threatens to negatively impact the ability for natural tissue remodeling and growth. Naturally derived materials, such as ECM structures including pericardium, have been shown to help define the microenvironment and signal the building of site appropriate functional tissue. ECM molecules represent a diverse set of structural and functional proteins and a variety of growth factors. Native binding sites from these molecules, as well as the formation of chemotactic cryptic peptides from parent molecules, can positively influence remodeling, recruit stem and progenitor cells, and modulate the immune response. These steps can ultimately determining the success of an implantable scaffold. If an ECM based hybrid biomaterial can be developed that promotes controlled regrowth of the injured site by avoiding crosslinking of the tissue, then the prosthetic can eventually be replaced with living tissue, and reduce subsequent surgical interventions.

The theory of calcification above suggests that if an alternative to GA can be developed that is effective at blocking enzymes and other immune activators, but avoids crosslinking of the tissue, then subsequent calcification of the material will be reduced. Thus, there is an ongoing and unmet need for improved compositions and methods for replacing and/or repairing malfunctioning or diseased cardiovascular and other tissues. The present disclosure meets this need.

SUMMARY OF THE DISCLOSURE

In an aspect, the present disclosure provides compositions comprising hybrid biomaterials.

In an embodiment, the hybrid biomaterials comprise: a) a compliant matrix dense tissue substrate, b) a first PPF layer comprising cross-linked poly(propylene fumarate) and/or cross-linked copolymer comprising a plurality of cross-linked propylene fumarate moieties; and c) a second PPF layer comprising cross-linked poly(propylene fumarate) and/or cross-linked copolymer comprising a plurality of cross-linked propylene fumarate moieties and a plurality of microparticles, a plurality of micropores, or both a plurality of microparticles and a plurality of micropores encapsulated within the cross-linked poly(propylene fumarate) and/or cross-linked copolymer comprising a plurality of cross-linked propylene fumarate moieties; where, the first PPF layer is disposed on at least a portion of a surface of the tissue substrate and the second PPF layer is disposed on at least a portion of a surface of the first PPF layer, or the second PPF layer is disposed on at least a portion of a surface of the tissue substrate and the first PPF layer is disposed on at least a portion of a surface of the second PPF layer.

In an embodiment, the cross-linked poly(propylene fumarate) or copolymer comprising a plurality of cross-linked propylene fumarate moieties of the hybrid biomaterial comprise a plurality of diethylfumarate (DEF) cross-linking moieties, N-vinylpyrollidone cross-linking moieties, or a combination of diethylfumarate cross-linking moieties and N-vinylpyrollidone cross-linking moieties.

In an embodiment, the microparticles of the hybrid biomaterial comprise poly(lactic-co-glycolic acid), poly(ethylene glycol), alginate, gelatin, collagen, poly(ethylene glycol), or a combination thereof.

In an embodiment, the microparticles of the hybrid biomaterial are 50 weight percent to 95 weight percent of the second PPF layer.

In an embodiment, the microparticles of the hybrid biomaterial comprise a bioactive material. In an embodiment, the bioactive material is selected from an antibiotic material, a cytokine, a growth factor, immunosuppressant material, and combinations thereof.

In an embodiment, the second PPF layer of the hybrid biomaterial further comprises a surfactant and the surfactant forms a layer at least partially disposed on a portion of a surface of one or more of the microparticles. In an embodiment, the surfactant is selected from polyvinyl alcohol, vitamin E, 1,2-Dioleoyl-sn-glycero-3-phosphocholine (DOPC), N-(Carbonyl-methoxypolyethyleneglycol 2000)-1,2-distearoyl-sn-glycero-3-phosphoethanolamine (DSPE-PEG), and 1,2-dioleoyl-3-trimethylammonium-propane (DOTAP), and combinations thereof.

In an embodiment, the compliant matrix dense tissue substrate of the hybrid biomaterial has a thickness of 300 micrometers to 1 millimeter and/or an area of 1,000 mm$^2$ to 1,000 cm$^2$.

In an embodiment, the first PPF layer and/or second PPF layer of the hybrid biomaterial has a thickness of 25 micrometers to 1 millimeter and/or an area of 1,000 mm$^2$ to 1,000 cm$^2$.

In an embodiment, the poly(propylene fumarate) of the hybrid biomaterial has a molecular weight of 500 to 4,000 g/mol.

In an aspect, the present disclosure provides methods of making hybrid biomaterials.

In an embodiment, the method of making the hybrid biomaterials comprise: a) providing an alcohol-dehydrated compliant matrix dense tissue substrate; b) coating at least a portion of the substrate with a first mixture comprising poly(propylene fumarate) or copolymer comprising a plurality of propylene fumarate moieties, a cross-linking agent, a photoinitiator, and a plurality of microparticles or a second mixture comprising poly(propylene fumarate) or copolymer comprising a plurality of propylene fumarate moieties, a cross-linking agent, and a photoinititor; c) exposing the coated substrate from b) to ultraviolet light such that the poly(propylene fumarate) or copolymer comprising a plurality of propylene fumarate moieties is crosslinked, d) if the first mixture is used in b), then coating the substrate from c) with the second mixture, e) exposing the coated substrate from d) to ultraviolet light such that the poly(propylene fumarate) or copolymer comprising a plurality of propylene fumarate moieties is crosslinked to provide the hybrid biomaterial, f) if the second mixture is used in b), then coating the substrate from c) with the first mixture, and g) exposing the coated substrate from d) to ultraviolet light such that the poly(propylene fumarate) or copolymer comprising a plurality of propylene fumarate moieties is crosslinked to provide the hybrid biomaterial. In an embodiment, the method of making the hybrid biomaterial further comprises the steps of: h) coating at least a portion of the product of g) with a first mixture comprising poly(propylene fumarate) or copolymer comprising a plurality of propylene fumarate moieties, a cross-linking agent, a photoinitiator, and a plurality of microparticles or a second mixture comprising poly(propylene fumarate) or copolymer comprising a plurality of propylene fumarate moieties, a cross-linking agent, and a photoinititor; i) exposing the coated substrate from h) to ultraviolet light such that the poly(propylene fumarate) or copolymer comprising a plurality of propylene fumarate moieties is crosslinked, j) if the first mixture is used in h), then coating the substrate from i) with the second mixture, k) exposing the coated substrate from j) to ultraviolet light such that the poly(propylene fumarate) or copolymer comprising a plurality of propylene fumarate moieties is crosslinked to provide the hybrid biomaterial, l) if the second mixture is used in h), then coating the substrate from i) with the first mixture, and m) exposing the coated substrate from j) to ultraviolet light such that the poly(propylene fumarate) or copolymer comprising a plurality of propylene fumarate moieties is crosslinked to provide the hybrid biomaterial; n) optionally, repeating steps h-n to provide additional layers to the substrate. In an embodiment, the method further comprises the removal of one or more of the microparticles from the hybrid biomaterial.

In an embodiment, the cross-linking agents of the method is selected from diethylfumarate (DEF), N-vinylpyrrolidone, and combinations thereof.

In an embodiment, one or more of the exposing the coated substrate to ultraviolet light is carried out for 1 minute to 180 minutes at a surface power density of 1 to 10 mW/cm$^2$.

In an aspect, the present disclosure provides methods for repairing a tissue defect in an individual.

In an embodiment the method for repairing a tissue defect in an individual comprises implanting in a region of the individual a hybrid biomaterial comprising: a) a compliant matrix dense tissue substrate; b) first PPF layer comprising cross-linked poly(propylene fumarate) and/or cross-linked copolymer comprising a plurality of cross-linked propylene fumarate moieties, and c) optionally, a second PPF layer comprising cross-linked poly(propylene fumarate) and/or cross-linked copolymer comprising a plurality of cross-linked propylene fumarate moieties and a plurality of microparticles, a plurality of micropores, or both a plurality of microparticles and a plurality of micropores encapsulated within the cross-linked poly(propylene fumarate) and/or cross-linked copolymer comprising a plurality of cross-linked propylene fumarate moieties, where the hybrid biomaterial is less immunogenic than a reference material, where, if only the first PPF layer is present, the first PPF layer is disposed on at least a portion of a surface of the substrate, if the first PPF layer and second PPF layer are present, the first PPF layer is disposed on at least a portion of a surface of the tissue substrate and the second PPF layer is disposed at least a portion of a surface of the first layer, or the second PPF layer is disposed on at least a portion of a surface of the tissue substrate and the first PPF layer is disposed on at least a portion of a surface of the first layer.

In an embodiment, the microparticles of the method for repairing a tissue defect in an individual comprise a bioactive material and the bioactive material is released into the individual. In an embodiment, the bioactive material is selected from an antibiotic material, a cytokine, a growth factor, immunosuppressant material, and combinations thereof.

BRIEF DESCRIPTION OF THE FIGURES

The patent or application file contains at least one drawing executed in color. Copies of this patent or patent application publication with the color drawings will be provided by the Office upon request and payment of the necessary fee.

Figure 13:
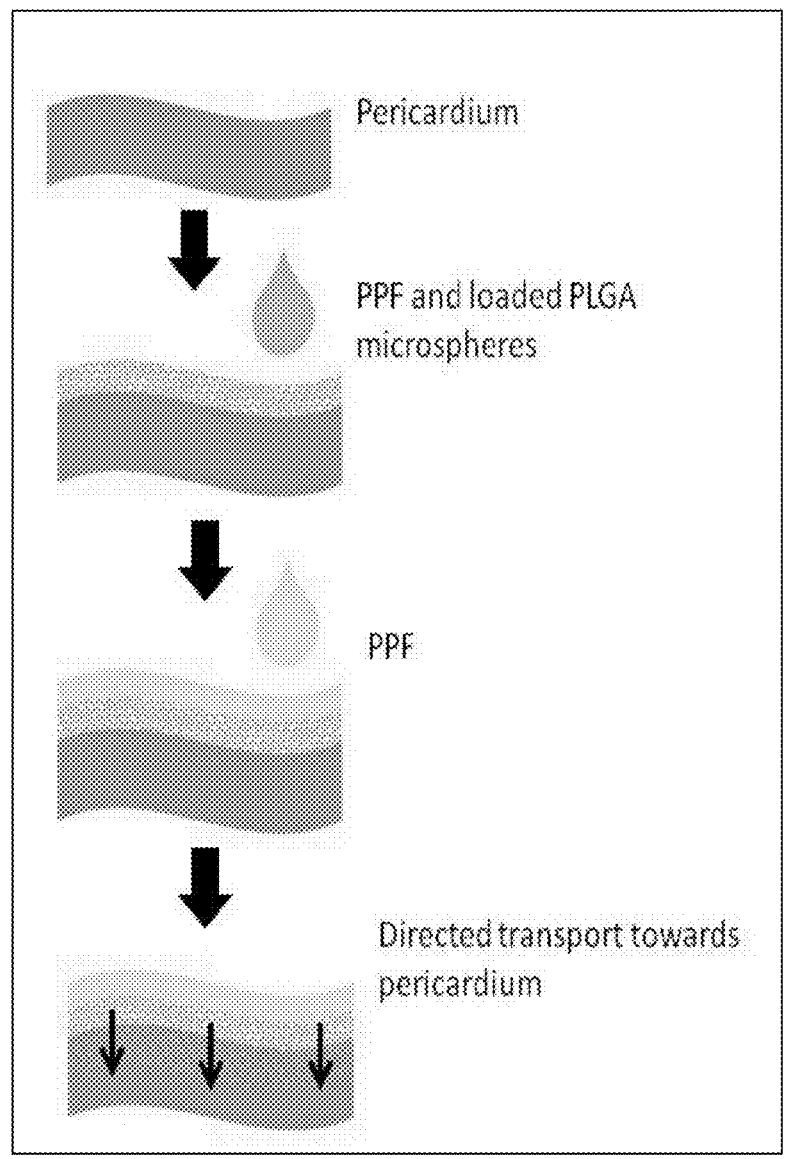

FIG. 13. Diagram of layered hybrid biomaterial of pericardium and PPF with embedded microparticle depots within the first PPF layer. The relatively quick degrading poly(lactic-co-glycolic) (PLGA) microparticles deliver bioactive factors to the pericardium substrate from within the PPF scaffold. As PLGA microparticles degrade hydrolytically and release encapsulated cargo, the PPF scaffold will retain strength and support of the pericardium substrate through remodeling FIG. 14. A) Degradation of PLGA and PPF. PLGA microparticles were degraded in groups of 4 mg of particles in 5 mL PBS over 21 days at 37 C. Number average molecular weight was measured using GPC, n=3 per time point. PPF thin films were degraded in 5 mL PBS over 150 days (not shown). Films were oven dried and compared to original mass to obtain % remaining, n=6 per time point. B) Release kinetics from PLGA particles in solution and PLGA particles in PPF thin films. OVA release from particles was measured using a Bradford assay at each time point, n=5.

Figure 15:
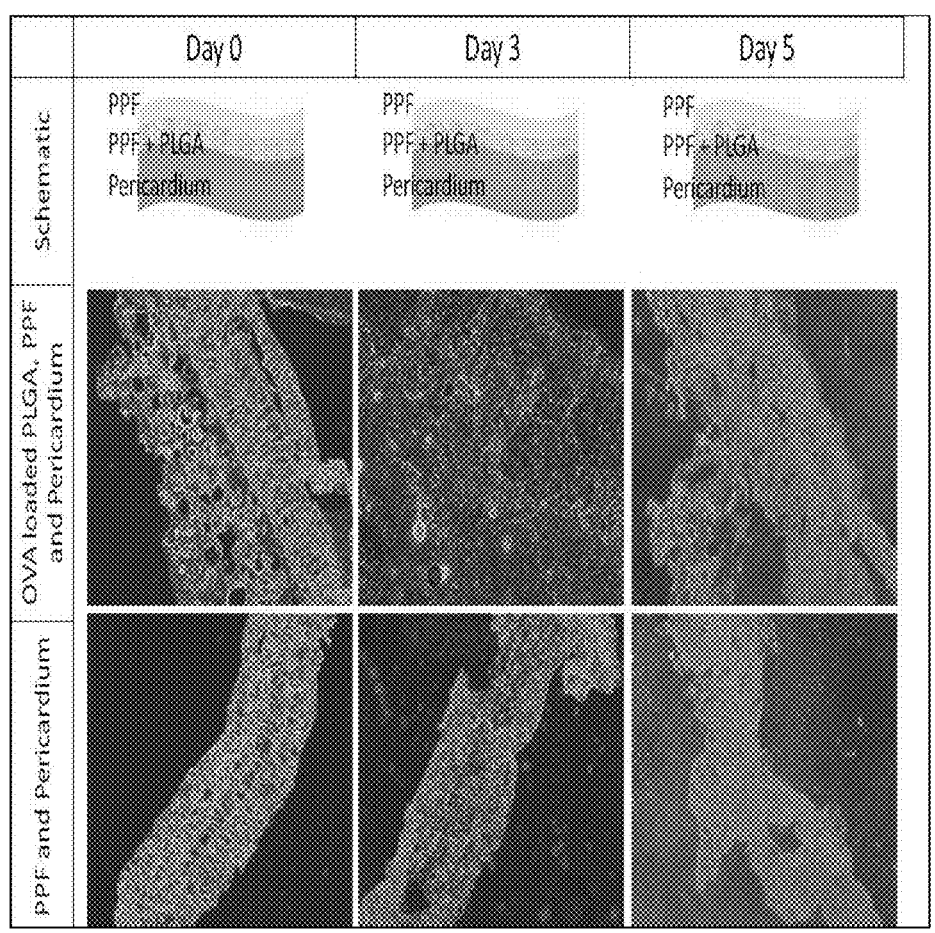

FIG. 15. Immunohistochemical Analysis of OVA Delivery in PPF/PLGA/Pericardium Samples. Pericardium tissue samples coupled with OVA-loaded PLGA/PPF or with just PPF were stained using an antibody for OVA, indicated with a localized blue stain. Staining shows OVA contained primarily in the polymer layer on day 0, moving into the pericardium tissue by day 5. There is very low blue fluorescence observed in the PPF and pericardium samples, corresponding to the absence of OVA.

DESCRIPTION OF THE DISCLOSURE

The present disclosure provides a hybrid biomaterial. The present disclosure also provides methods of making hybrid biomaterials and methods of using hybrid biomaterials.

The present disclosure is based on a novel combination of a synthetic polymer and natural biomaterial. By incorporating these two entities, both a mechanical support for the tissue through remodeling and growth processes from the polymer component, as well as a biological signaling and remodeling platform from the biological component are provided. The result is an innovative design of material that can create a lasting solution through the eventual formation of native site appropriate tissue.

In an aspect, the present disclosure provides hybrid biomaterials. The hybrid biomaterials comprise one or more layers of cross-linked poly(propylene fumarate) and/or cross-linked copolymer comprising a plurality of cross-linked propylene fumarate moieties. The layers of cross-linked poly(propylene fumarate) and/or cross-linked copolymer comprising a plurality of cross-linked propylene fumarate moieties are disposed on a substrate (e.g., a compliant matrix dense tissue substrate) and/or another layer of cross-linked poly(propylene fumarate) and/or cross-linked copolymer comprising a plurality of cross-linked propylene fumarate moieties. One or more of the layers of cross-linked poly(propylene fumarate) and/or cross-linked copolymer comprising a plurality of cross-linked propylene fumarate moieties may, at each occurrence in the hybrid biomaterials, further comprise a plurality of microparticles, a plurality of micropores, or both microparticles and micropores encapsulated within the cross-linked poly(propylene fumarate) and/or cross-linked copolymer comprising a plurality of cross-linked propylene fumarate moieties. In an embodiment, the hybrid biomaterial is made by a method of the present disclosure.

In an embodiment, a hybrid biomaterial comprises: a) a compliant matrix dense tissue substrate; b) a first PPF layer comprising cross-linked poly(propylene fumarate) and/or cross-linked copolymer comprising a plurality of cross-linked propylene fumarate moieties; and c) a second PPF layer comprising cross-linked poly(propylene fumarate) and/or cross-linked copolymer comprising a plurality of cross-linked propylene fumarate moieties and a plurality of microparticles, a plurality of micropores, or both microparticles and micropores encapsulated within the cross-linked poly(propylene fumarate) and/or cross-linked copolymer comprising a plurality of cross-linked propylene fumarate moieties. The first PPF layer is disposed on at least a portion of a surface of the tissue substrate and the second PPF layer is disposed on at least a portion of a surface of the first PPF layer or the second PPF layer is disposed on at least a portion of a surface of the tissue substrate and the first PPF layer is disposed on at least a portion of a surface of the second PPF layer.

A variety of compliant matrix dense tissue substrates can be used. The substrates comprise, for example, ECM-rich, membrane-like tissues. The substrates may comprise bulk tissues. The substrate materials are compatible with PPF or copolymers comprising propylene fumarate moieties. Examples of suitable substrate materials include skin, vasculature, periosteum, and skeletal muscle. The substrate material can be obtained from an animal (a human or non-human animal such as a bovine). In an embodiment, the substrate is pericardium tissue. In an embodiment the substrate is an alcohol dehydrated compliant matrix dense tissue substrate.

The hybrid biomaterial can comprise one or more layers comprising cross-linked poly(propylene fumarate) and/or cross-linked copolymer comprising a plurality of cross-linked propylene fumarate moieties (e.g., PPF layers such as first PPF layers or second PPF layers). One of the layers is disposed on a compliant matrix dense tissue substrate. Each layer is disposed on at least a portion or all of the layer immediately beneath it (e.g., a substrate or other layer of cross-linked poly(propylene fumarate) and/or cross-linked copolymer comprising a plurality of cross-linked propylene fumarate moieties) in the material (if the substrate is considered the bottom of the structure) or the substrate.

In an embodiment, a layer of cross-linked poly(propylene fumarate) and/or cross-linked copolymer comprising a plurality of cross-linked propylene fumarate moieties (e.g., a first PPF layer) is disposed on a compliant matrix dense tissue substrate and a layer of cross-linked poly(propylene fumarate) and/or cross-linked copolymer comprising a plurality of cross-linked propylene fumarate moieties that also comprises a plurality of microparticles, a plurality of micropores, or both microparticles and micropores encapsulated within the cross-linked poly(propylene fumarate) and/or cross-linked copolymer comprising a plurality of cross-linked propylene fumarate moieties (e.g., a second PPF layer) is disposed on the aforementioned layer of cross-linked poly(propylene fumarate) and/or cross-linked copolymer comprising a plurality of cross-linked propylene fumarate moieties (e.g., the second PPF layer). The order of the PPF layers on the substrate may be reversed. Accordingly, in an embodiment, a layer of cross-linked poly(propylene fumarate) and/or cross-linked copolymer comprising a plurality of cross-linked propylene fumarate moieties that also comprises a plurality of microparticles, a plurality of micropores, or both microparticles and micropores encapsulated within the cross-linked poly(propylene fumarate) and/or cross-linked copolymer comprising a plurality of cross-linked propylene fumarate moieties (e.g., a second PPF layer) is disposed on the substrate and a layer of cross-linked poly(propylene fumarate) and/or cross-linked copolymer comprising a plurality of cross-linked propylene fumarate moieties (e.g., a first PPF layer) is disposed on the aforementioned layer of cross-linked poly(propylene fumarate) and/or cross-linked copolymer comprising a plurality of cross-linked propylene fumarate moieties that also comprises a plurality of microparticles, a plurality of micropores, or both microparticles and micropores encapsulated within the cross-linked poly(propylene fumarate) and/or cross-linked copolymer comprising a plurality of cross-linked propylene fumarate moieties (e.g., the second PPF layer). The compliant matrix dense tissue can have various thicknesses and coverage areas (e.g., sizes and shapes). For example, the compliant matrix dense tissue substrate has a thickness of 300 micrometers to 1 millimeter, including all integer micrometer values and ranges therebetween, and/or a coverage area of 1,000 $mm^2$ to 1,000 $cm^2$, including all integer $mm^2$ values and ranges therebetween.

In an embodiment, the hybrid biomaterial comprises one, two, three, or four layers of cross-linked poly(propylene fumarate) and/or cross-linked copolymer comprising a plurality of cross-linked propylene fumarate moieties (e.g., first PPF layers or second PPF layers) and one, two, three or four of the layers may further comprise a plurality of microspheres and/or a plurality of micropores.

The layer(s) are crosslinked by cross-linking moieties. The cross-linking moieties (i.e. plurality of cross-linked propylene fumarate moieties) can be derived from/formed from cross-linking agents. For example, the cross-linking agent is diethylfumarate (DEF) and the crosslinking moieties are diethylfumarate cross-linking moieties, the cross-linking agent is N-vinylpyrollidone and the cross-linking moieties are N-vinylpyrollidone cross-linking moieties. The hybrid biomaterial can comprise a combination of one or more diethylfumarate cross-linking moieties and one or more N-vinylpyrollidone cross-linking moieties. In an embodiment, the hybrid biomaterial comprises cross-linked poly(propylene fumarate) or copolymer comprising a plurality of cross-linked propylene fumarate moieties comprising a plurality of diethylfumarate (DEF) cross-linking moieties, N-vinylpyrollidone cross-linking moieties, or a combination of diethylfumarate cross-linking moieties and N-vinylpyrollidone cross-linking moieties.

When describing a moiety as "cross-linked," the name of the moiety refers to the precursor rather than the product. For example, "cross-linked propylene fumarate" refers to a precursor propylene fumarate moiety that has undergone cross-linking with a cross-linking agent (e.g., DEF), or another propylene fumarate moiety. For example, when a propylene fumarate moiety undergoes cross-linking with a cross-linking agent, such as DEF, a carbon of the carbon-carbon double bond of the propylene fumarate moiety and a carbon of the carbon-carbon double bond of the DEF moiety become covalently cross linked, resulting in a crosslinked succinate product.

The following is depicts examples of the relationship between several cross-linking agents and cross-linking moieties:

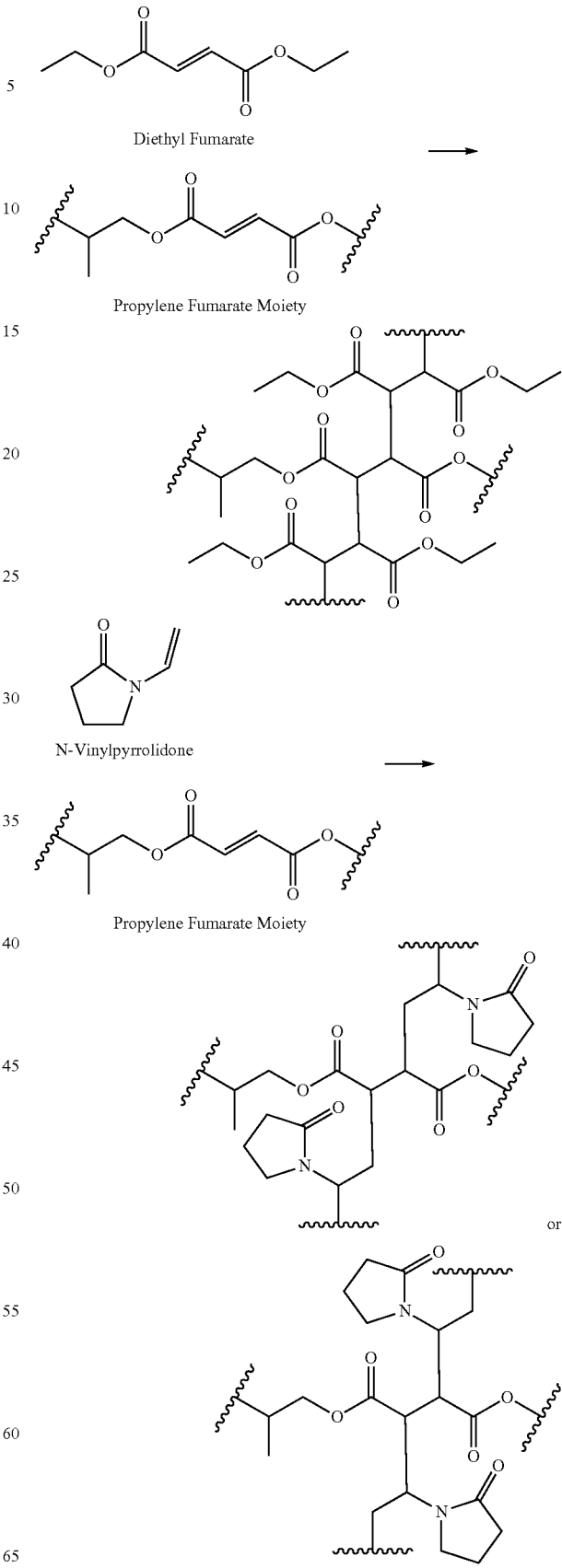

The cross-linking agent can react with one or both of the carbons of the carbon-carbon double bonds of the fumarate moiety. These examples are merely illustrative and one having skill in the art would recognize that cross-linking moieties may have different regioisomers and that these cross-linking moieties in particular can have different regioisomers.

The layer(s) of the hybrid biomaterial may comprise one or more (e.g., a plurality) of microparticles and/or one or more (e.g., a plurality of micropores). The microparticle(s) and/or micropore(s) is/are encapsulated within the cross-linked poly(propylene fumarate) and/or cross-linked copolymer comprising a plurality of cross-linked propylene fumarate moieties. The microparticles are compatible (i.e., able to be incorporated into uncrosslinked PPF in a homogenous or otherwise controlled presence and are not damaged by or do not prevent UV crosslinking) with the poly(propylene fumarate) or copolymer comprising a plurality of cross-linked propylene fumarate moieties.

The microparticles comprise, for example, poly(lactic-co-glycolic acid), alginate, gelatin, collagen, poly(ethylene glycol) (e.g., poly(ethylene glycol) having a molecular weight of 100 to 50,000 g/mol) or a combination thereof. The microparticles can be formed from these materials. The microparticles can be formed by methods known in the art.

The microparticles can have various sizes. For example, the microparticles are generally spherical and have a diameter in the micron range. In an embodiment, the microparticles have a size (e.g., a longest dimension or diameter) of 1 to 100 microns, including all integer micron values and ranges therebetween. The microparticles, when present, are at least 50% or more by weight of the layer comprising cross-linked poly(propylene fumarate) and/or cross-linked copolymer comprising a plurality of cross-linked propylene fumarate moieties. In an embodiment, a layer comprising cross-linked poly(propylene fumarate) and/or cross-linked copolymer comprising a plurality of cross-linked propylene fumarate moieties has 50% by weight to 95% by weight (based on the weight of cross-linked poly(propylene fumarate) and/or cross-linked copolymer comprising a plurality of cross-linked propylene fumarate moieties) microparticles, including all integer % by weight values and ranges therebetween.

Microparticle(s) may comprise a bioactive material. Examples of suitable bioactive materials include antibiotic materials, cytokines, growth factors, immunosuppressant materials. Examples of antibiotics include doxycycline, tetracycline hydrochloride, rifampin, tobramycin, colistin, tigecycline. Examples of cytokines include interleukin 4 (IL 4), interleukin 10 (IL 10), interleukin 1. Examples of growth factors include stromal cell derived factor 1 (SDF), transforming growth factor beta 1 (TGFβ1) and basic fibroblast growth factor (bFGF), vascular endothelial growth factor (VEGF), tumor necrosis factor alpha (TNFα), bone morphogenic protein 2 (BMP2), platelet derived growth factor (PDGF). Examples of immunosuppressants comprise cyclosporine A, dexamethasone. Microparticle(s) can have combinations of two or more bioactive materials. Bioactive materials are present between 0.05-20,000 ng per mg of microparticles.

A layer having a plurality of micropores can be derived from a layer having microparticles. For example, a portion or all of the microparticles in a layer can be removed or degrade away to provide a layer comprising micropores or a combination of microparticles and micropores.

Layer(s) comprising cross-linked poly(propylene fumarate) and/or cross-linked copolymer comprising a plurality of cross-linked propylene fumarate moieties and microparticles further comprises a surfactant. The surfactant is disposed on/forms a layer at least partially disposed on a portion of a surface of one or more of the microparticles. Without intending to be bound by any particular theory, it is considered that the surfactant stabilizes a microparticle. Examples of suitable surfactants include polyvinyl alcohols, vitamin E, 1,2-Dioleoyl-sn-glycero-3-phosphocholine (DOPC), N-(Carbonyl-methoxypolyethyleneglycol 2000)-1,2-distearoyl-sn-glycero-3-phosphoethanolamine (DSPE-PEG), and 1,2-dioleoyl-3-trimethylammonium-propane (DOTAP). The layer(s) can comprise combinations of two or more surfactants. Suitable surfactants are commercially available or can be made by methods known in the art.

Layer(s) comprising cross-linked poly(propylene fumarate) and/or cross-linked copolymer comprising a plurality of cross-linked propylene fumarate moieties can have various thickness and areas. For example, the layer(s) (e.g., first PPF layer and/or second PPF layer) has a thickness of 25 micrometers to 1 millimeter, including all integer micrometer values and ranges therebetween, and/or an area of 1,000 $mm^2$ to 1,000 $cm^2$, including all integer $mm^2$ values and ranges therebetween.

The hybrid biomaterials can have desirable properties. For example, the hybrid biomaterial can have desirable elastic modulus and/or yield strength. In an embodiment, the hybrid biomaterial has elastic modulus and/or yield strength that is equivalent or better than a GA treated substrate material, where the substrate material is the same as that of the hybrid biomaterial. The method of combining a polymer of the present disclosure and a compliant matrix dense tissue substrate does not chemically or physically alter the tissue substrate (i.e., the polymer is non-covalently bound to the tissue substrate). This allows cells to recognize the natural biologic components of the tissue.

In an aspect, the present invention provides methods of making hybrid biomaterials (e.g., hybrid biomaterials of the present disclosure). The methods are based on cross-linking a layer of poly(propylene fumarate) or copolymer comprising a plurality of cross-linked propylene fumarate moieties. The layer is disposed on a compliant matrix dense tissue substrate or a cross-linked layer of poly(propylene fumarate) or cross-linked layer of copolymer comprising a plurality of cross-linked propylene fumarate moieties. The layer may have a plurality of microspheres encompassed in the poly (propylene fumarate) or copolymer comprising a plurality of cross-linked propylene fumarate moieties. The cross-linking steps may be repeated multiple times to provide multi layered structures.

In an embodiment, a method of making a hybrid biomaterial (e.g., a hybrid biomaterial of the present disclosure) comprises: a) providing an alcohol-dehydrated compliant matrix dense tissue substrate; b) coating at least a portion of the substrate with a first mixture comprising poly(propylene fumarate) and/or copolymer comprising a plurality of propylene fumarate moieties, a cross-linking agent, a photoinitiator, and a plurality of microparticles or a second mixture comprising poly(propylene fumarate) or copolymer comprising a plurality of propylene fumarate moieties, a cross-linking agent, and a photoinititor; c) exposing the coated substrate from b) to ultraviolet light such that the poly (propylene fumarate) or copolymer comprising a plurality of propylene fumarate moieties is crosslinked, d) if the first mixture is used in b), then coating the substrate from c) with the second mixture, e) exposing the coated substrate from d) to ultraviolet light such that the poly(propylene fumarate) or copolymer comprising a plurality of propylene fumarate moieties is crosslinked to provide the hybrid biomaterial, f) if the second mixture is used in b), then coating the substrate from c) with the first mixture, and g) exposing the coated substrate from d) to ultraviolet light such that the poly (propylene fumarate) or copolymer comprising a plurality of propylene fumarate moieties is crosslinked to provide the hybrid biomaterial. This embodiment may further comprise repeating steps as necessary to provide additional cross-linked PPF layers.

It is desirable to use an alcohol-dehydrated compliant matrix dense tissue substrate. For example, the substrate is an alcohol dehydrated pericardium tissue substrate. An alcohol-dehydrated compliant matrix dense tissue substrate can be formed by contacting a compliant matrix dense tissue substrate (e.g., a pericardium tissue substrate) with a composition comprising an alcohol or mixture of alcohols. Examples of suitable alcohols include methanol, ethanol, and propanols. In an embodiment, a compliant matrix dense tissue substrate (e.g., a pericardium tissue substrate) is contacted with ethanol to provide an alcohol-dehydrated compliant matrix dense tissue substrate (e.g., an alcohol-dehydrated pericardium tissue substrate). In an embodiment the alcohol-dehydrated compliant matrix dense tissue substrate is formed by treating the compliant matrix dense tissue substrate with increasing concentrations of alcohol for 5-20 minutes for each concentration of alcohol used at room temperature. In an embodiment the compliant matrix dense tissue substrate is immersed in a 20% alcohol solution for 5-20 minutes, followed by immersion in a 40% alcohol solution for 5-20 minutes, followed by a 60% alcohol solution for 5-20 minutes, followed by a 80% alcohol solution for 5-20 minutes, followed by immersion in 100% alcohol. In an embodiment the alcohol used is ethanol.

The poly(propylene fumarate) and copolymers comprising propylene fumarate moieties have one or more photo-crosslinkable groups. A covalently cross-linked network is formed on crosslinking of a plurality of photocrosslinkable groups and/or photocrosslinking a plurality of photocrosslinkable groups with a cross-linking agent. It is desirable that the poly(propylene fumarate) and copolymers comprising propylene fumarate moieties are a viscous liquid that can be used to form a layer on the substrate or a layer of cross-linked poly(propylene fumarate) and/or cross-linked copolymer comprising propylene fumarate moieties.

The poly(propylene fumarate) can be made by methods known in the art. The poly(propylene fumarate) (e.g., individual polymer chains of the polypropylene fumarate) can have a range of molecular weights (e.g., Mw and/or Mn). For example, the poly(propylene fumarate) (e.g., the individual polymer chains of the poly(propylene fumarate)) has a molecular weight (Mn) of 500 to 4,000 g/mol, including all integer g/mol values and ranges therebetween.

Copolymers comprising propylene fumarate moieties are commercially available and can be made by methods known in the art. For example, the copolymers are block copolymers, random copolymers, or alternating copolymers. The copolymers comprising propylene fumarate moieties (e.g., individual polymer chains of the copolymer) can have a range of molecular weights (e.g., Mw and/or Mn). For example, the copolymers comprising propylene fumarate moieties (e.g., individual polymer chains of the copolymer) have a molecular weight (Mn) of 1,000 to 100,000 g/mol, including all integer g/mol values and ranges therebetween.

The copolymers can have, in addition to propylene fumarate moieties, for example, poly(caprolactone) or caprolactone moieties, poly(ethylene glycol) or ethylene glycol moieties, poly(lactic-co-glycolic acid) (PLGA) moieties. Examples of suitable copolymers include poly(caprolactone-co-propylene fumarate), poly(propylene glycol)-co-propylene fumarate, poly(lactic-co-glycolic acid)-co-propylene fumarate. A layer may have a combination poly (propylene fumarate) and copolymers comprising propylene fumarate moieties. The copolymers can have desirable properties such as improved (relative to poly(propylene fumarate)) biodegradability, water swelling, and mechanical properties.

In the case of copolymers having propylene fumarate moieties and poly(ethylene glycol) or ethylene glycol moieties, -[—OCH$_2$CH$_2$—]-, (e.g., poly(ethylene glycol)-co-propylene fumarate), these co-polymers can have, for example, one or more poly(ethylene glycol) oligomer moieties (e.g., one or more poly(ethylene glycol) oligomer moieties having a molecular weight of about 88 g/mol (two ethylene glycol repeat units) to about 9,900 g/mol (225 ethylene glycol repeat units)). These copolymers can be referred to as poly(propylene fumarate)-oligo(ethylene glycol). The copolymers having propylene fumarate moieties and poly(ethylene glycol) or ethylene glycol moieties (e.g., poly(ethylene glycol)-co-propylene fumarate) can also have, for example, ethylene glycol moieties totaling a molecular weight of about 10,000 (226 ethylene glycol units) to about 99,000 (2250 ethylene glycol units).

The mixtures comprise one or more cross-linking agents. The cross-linking agents can react with carbon-carbon double bonds of propylene fumarate moieties in the poly (propylene fumarate) or copolymer comprising a plurality of propylene fumarate moieties. Examples of suitable cross-linking agents include diethylfumarate (DEF), and N-vinylpyrollidone. The cross-linking agent(s) are present in the mixtures, for example, at 0 to 50 weight percent, including all 0.01 weight percent values and ranges therebetween, of the mixture. In an embodiment, the cross-linking agent(s) are present in the mixtures, for example, at 0.01 to 50 weight percent, including all 0.01 weight percent values and ranges therebetween, of the mixture. Suitable cross-linking agents are commercially available and can be made by methods known in the art.

The mixtures comprise one or more photoinitiators. On exposure of the mixture to ultraviolet radiation, the photoinitiators initiate the cross-linking reaction. Examples of suitable photoinitiators include acylphoshine photoinitiators such as bis-acyl phosphine oxide photoinitiators (BAPOs), for example, (bis-2,4,6-trimethylbenzoyl)-phosphine oxide, and monoacylphosphine oxide photoinitiators (MAPOs), for example, diphenyl(2,4,6-trimethylbenzoyl)phosphine oxide (TPO). Suitable photoinitiators are known in the art. The photoinitiators are present in the mixtures, for example, at 0.01 to 0.9 weight percent, including all 0.01 weight percent values and ranges therebetween, of the mixture. The photoinitiators can be added to a mixture as a solution in solvent, such as, for example, methylene chloride or acetone. Suitable photoinitiators are commercially available and can be made by methods known in the art.

The mixtures are coated on a compliant matrix dense tissue substrate or another layer comprising cross-linked poly(propylene fumarate) and/or cross-linked copolymer comprising a plurality of cross-linked propylene fumarate moieties by various methods. For example, a mixture is coated on a substrate or another layer by painting (i.e., applying a liquid polymer using a brush), deposited via droplets, or printed using inkjet technology or stereolithography.

A layer comprising a mixture is exposed to ultraviolet radiation (e.g., radiation having a wavelength or wavelengths in the range of 220 nm to 400 nm) to provide a desired number of crosslinks (i.e., cross-linking moieties). The exposure is carried out without substantial damage (or no damage) to the substrate or other layer(s). Generally, higher doses of ultraviolet radiation (e.g., longer exposure time and/or higher surface power density) provide higher numbers of crosslinks. Thicker films comprising poly(propylene fumarate) and/or copolymer comprising a plurality of propylene fumarate moieties generally require higher doses of ultraviolet radiation to provide the same number of crosslinks as compared to a thinner film of the same poly (propylene fumarate) and/or copolymer. Also, higher amounts of photoinitiator may allow for shorter exposure time and/or surface power density to provide a desired number of crosslinks. For example, a substrate coated with a mixture comprising poly(propylene fumarate) and/or copolymer comprising a plurality of propylene fumarate moieties is exposed to ultraviolet radiation for 1 minute to 180 minutes, including all integer number of minutes and ranges therebetween, and/or at a surface power density of 1 to 10 mW/cm$^2$, including all integer number of mW/cm$^2$ values and ranges therebetween.

The methods may further comprise removing one or more of the microparticles from the hybrid biomaterial (e.g., from one or more of the one or more layers comprising cross-linked poly(propylene fumarate) and/or cross-linked copolymer comprising a plurality of cross-linked propylene fumarate moieties). Removal of one or more of the microparticles provides a hybrid biomaterial comprising layer(s) comprising cross-linked poly(propylene fumarate) and/or cross-linked copolymer comprising a plurality of cross-linked propylene fumarate moieties and a plurality of micropores, and, optionally, a plurality of microparticles. The micropores have substantially the same or the same size and morphology as the microparticles that are removed to provide the micropores. By substantially the same, all of the dimensions of the micropores deviate 5% or less from the microparticles from which they are formed. The micropores can be removed from a layer by hydrolysis (e.g., contacting a layer with an aqueous solvent), enzymatic degradation, and/or contacting the layer with a calcium chelator (e.g., ethylenediaminetetraacetic acid). For example, some or all of the PLGA microparticles in a layer are removed by hydrolysis, some or all of the alginate microparticles are removed by contacting the layer with a calcium chelator (e.g., ethylenediaminetetraacetic acid), and/or some or all of the collagen microparticles are removed by enzymatic dehydration. Selection of removal conditions is within the purview of one having skill in the art. Where two or more types of microparticles are present in a layer, one or more types of microparticles can be selectively removed.

In an aspect, the present disclosure provides uses of hybrid biomaterials (e.g., hybrid biomaterials of the present disclosure). For example, the hybrid biomaterials are used to repair a tissue defect (e.g., a tear or a hole in a tissue) in an individual. The hybrid biomaterials may be desirable for this use based on their biodegradability and/or ability to release bioactive materials at the repair site.

In an embodiment, a method for repairing a tissue defect in an individual comprises implanting in a region of the individual a hybrid biomaterial of the present disclosure. In another embodiment, a method for repairing a tissue defect in an individual comprises implanting in a region of the individual a hybrid biomaterial comprising: a) a compliant matrix dense tissue substrate; b) first PPF layer comprising cross-linked poly(propylene fumarate) and/or cross-linked copolymer comprising a plurality of cross-linked propylene fumarate moieties, and c) optionally, a second PPF layer comprising cross-linked poly(propylene fumarate) and/or cross-linked copolymer comprising a plurality of cross-linked propylene fumarate moieties and a plurality of microparticles, micropores, or both microparticles and micropores encapsulated within the cross-linked poly(propylene fumarate) and/or cross-linked copolymer comprising a plurality of cross-linked propylene fumarate moieties. The hybrid biomaterial may be less immunogenic than a reference material. If only the first PPF layer is present, the first PPF layer is disposed on at least a portion of a surface of the substrate. If the first PPF layer and second PPF layer are present, the first PPF layer is disposed on at least a portion of a surface of the tissue substrate and the second PPF layer is disposed at least a portion of a surface of the first PPF layer or, if the second PPF layer is disposed on at least a portion of a surface of the tissue substrate and the first PPF layer is disposed on at least a portion of a surface of the first layer.

The hybrid biomaterial used to repair a tissue defect in an individual may comprise a PPF layer comprising cross-linked poly(propylene fumarate) and/or cross-linked copolymer comprising a plurality of cross-linked propylene fumarate moieties and a plurality of microparticles, micropores, or both microparticles and micropores encapsulated within the cross-linked poly(propylene fumarate) and/or cross-linked copolymer comprising a plurality of cross-linked propylene fumarate moieties.

In an embodiment, the hybrid biomaterial is less immunogenic than a reference material or any other suitable reference, i.e., any suitable control. In various embodiments, the reference is untreated compliant dense matrix tissue substrate (e.g., untreated pericardium tissue substrate), or compliant dense matrix tissue substrate (e.g., a pericardium tissue substrate) treated with a composition that does not comprise PPF, such as compliant dense matrix tissue substrate (e.g., a pericardium tissue substrate) treated with GA but not PPF, or a value obtained from measuring such samples. Accordingly, the reference can be a known value or range of values, or may be a value or range of values determined from, for instance, one or more control or experimental samples. In some embodiments, the reference value is an average value determined from analysis of a number of samples with or without a PPF treatment according to this disclosure. In various embodiments, the reference comprises a statistical value, such as an area under a curve, or another area or plot on a graph.

By "less immunogenic" than a reference it is meant that a hybrid biomaterial (e.g., a PPF treated pericardium tissue substrate (with or without microspheres or microparticles) stimulate less of an immune response in an individual relative to the reference. The immune response includes but is not necessarily limited to a cell mediated immune response, a humoral immune response, or a combination thereof. In embodiments, the immune response that is dampened in an individual relative to a suitable reference comprises a reduced inflammatory response. Methods of determining inflammatory responses are well known in the art and include but are not necessarily limited to measuring proinflammatory cytokines (e.g., interleukin-1, tumor necrosis factor-α), adhesion molecules (e.g., intercellular adhesion molecule-1, selectins), inflammatory stimuli with hepatic effects (e.g., interleukin-6) or the products of the hepatic stimulation, such as C-reactive protein (CRP), and a multitude of other markers that will be such as an elevated leukocyte count. In certain embodiments, a material introduced to an individual exhibits less invasion by immune cells. In a non-limiting example, a material introduced into an individual according to this disclosure exhibits lower macrophage invasion relative to a reference. In embodiments, the macrophage are M1 macrophages. In embodiments, the presence, absence and/or amount of macrophage can be determined using any suitable approach, one non-limiting embodiment of which comprises immunohistochemistry using macrophage markers. In an embodiment, the macrophage cell surface antigen F4/80 is used. In an embodiment, a hybrid biomaterial introduced into an individual according to this disclosure exhibits the presence of macrophages that are homogenously spread through the implant or at least a portion of it. In contrast, a reference material, i.e., a pericardium material that does not comprise PPF and/or was not subjected to a PPF treatment would be expected to exhibit distinct and/or dense populations, such as macrophage cells surrounding the exterior of the implant.

In an embodiment, a hybrid biomaterial introduced into an individual according to this disclosure exhibits lower calcium deposition relative to a reference. Calcium deposition analysis can be performed using a wide variety of approaches that are known to those skilled in the art. In embodiments, the reference comprises a calcium deposition value obtained from an untreated control, or a control treated with GA, or a value or values obtained from analysis of such samples. In an embodiment the hybrid biomaterial has no more than 1 µg of calcium pre mg of tissue sample for at least 6 weeks after implantation in an individual. In an embodiment, the hybrid biomaterial does not have any observable calcium deposits for at least 6 weeks after implantation in an individual.

The individual into which a hybrid biomaterial of this disclosure can be introduced can be any animal. In embodiments the animal is a mammal. In embodiments the mammal is a human or non-human mammal.

The hybrid biomaterial can be used to repair a variety of tissue defects in an individual. For example, the hybrid biomaterial is used to repair a tear or hole in a wall of a luminal tissue (e.g., patch a vessel or intestinal wall), a heart valve, facie, or abdominal wall (e.g., a hernia). In another example, the hybrid biomaterial is used to replace a membranous tissue. In embodiments, the hybrid biomaterial is used to replace scarred or ischemic tissue. In an embodiment the hybrid biomaterial is used to replace tissue that is damaged by injury, disease, or defect.

The hybrid biomaterial may comprise microparticles comprising bioactive material(s) as described herein. For example, the bioactive materials comprise any one or any combination of an antibiotic material, a cytokine, a growth factor, or immunosuppressant material. The microparticles may degrade to release the bioactive material(s) at the tissue repair site in the individual.

The steps of the methods described in the various examples, embodiments, and examples disclosed herein are sufficient to produce the hybrid biomaterials of the present disclosure or carry out the methods of repairing a tissue defect in an individual. Thus, in an embodiment, a method of producing a hybrid biomaterial of the present disclosure or method of repairing a tissue defect consists essentially of a combination of the steps of the methods disclosed herein. In another embodiment, the method consists of such steps.

The following examples are presented to illustrate the present disclosure. They are not intended to be limiting in any manner.

Example 1

The following in an example of the preparation and characterization of a hybrid biomaterial of the present disclosure.

Previously known pericardium based cardiovascular devices are bound by a 10 year maximum lifetime due to detrimental calcification and degradation. A novel synthetic material was developed to create a lasting replacement for malfunctioning or diseased tissue in the cardiovascular system. This example couples PPF and a natural biomaterial together in a hybrid composite and evaluates the composite versus the standard glutaraldehyde treated tissue. The polymer reinforcement provided physical protection from proteolytic enzymes and degradation, but leave the original collagen and elastin matrix unaltered. Calcification rate and durability of the hybrid biomaterial were evaluated in vitro and in an in vivo subdermal animal model. Results demonstrated that PPF is an effective support and leads to significantly less calcium deposition, important metrics when evaluating cardiovascular material. By avoiding chemical crosslinking of the tissue and associated side effects, PPF reinforced pericardium as a hybrid biomaterial offers a promising potential direction for further development in cardiovascular material alternatives. Eliminating the basis for the majority of cardiovascular prosthetic failures could revolutionize expectations for extent of cardiovascular repair.

Applying a paintable polymer to the surface of pericardium tissue provided physical support and biological block to natural degradation, while leaving the original tissue unaltered. This resulted in a hybrid biomaterial that retained mechanical integrity but did not accumulate calcium deposits. For this purpose, the synthetic polymer poly(propylene fumarate) (PPF), was selected for its biocompatibility, biodegradability, and strength.

Poly(propylene fumarate), (PPF), is an unsaturated linear polyester that is crosslinkable through UV radiation with itself or with other compatible crosslinkers through the double bonds in fumarate. PPF is biodegradable by hydrolysis of ester bonds, and forms the naturally occurring byproducts fumaric acid and propylene glycol upon degradation. The degradation time is largely dependent on polymer characteristics such as molecular weight, crosslinker, and crosslinked density. The uncrosslinked polymer is viscous at room temperature, allowing it to be easily "painted" onto a surface. In addition, PPF viscosity can be reduced, without significantly altering the components of the system, with the addition of diethyl fumarate (DEF), the monomer from which PPF is synthesized. The addition of DEF to PPF can also cause variations in the crosslinked biomaterial's mechanical strength, and can be utilized as a parameter to tune the characteristics of the hybrid biomaterial.

The first aim was to identify measurable mechanical properties of natural pericardium and develop a composition of PPF to mirror those properties. The designed composition of the polymer was then married to the pericardium tissue, and the hybrid biomaterial was evaluated on two fronts. The first evaluation of the hybrid biomaterial was to test if PPF reinforcement was an effective support for natural pericardium enzymatic degradation. The second evaluation of the hybrid biomaterial was to investigate if PPF reinforced pericardium would cause minimal calcification when compared to the GA treated standard. Performance in these two areas will support the hypothesis that a topically applied polymer can biologically and mechanically support pericardium for use in cardiovascular applications.

Methods. Polymer Synthesis and Composition. PPF was synthesized by a two-step process as previously described. Briefly, propylene glycol and diethyl fumarate were combined in a 3:1 molar ratio. Zinc chloride, acting as a catalyst, and hydroquinone, as a radical inhibitor, were added in a 0.01:0.002 molar ratio. The reaction was carried out under nitrogen flow, producing ethanol as a byproduct and bis(hydroxypropyl) fumarate as the intermediate. Next, under vacuum, transesterification of the intermediate produces PPF with propylene glycol as a byproduct. Gel permeation chromatography was used to calculate the number average molecular weight (Mn) and polydispersity index (PDI) of the purified PPF. For use in this study, PPF (Mn 1150 and PDI 1.6) was mixed with the monomer DEF, and then mixed with the photoinitiator bis(2,4,6-trimethylbenzoyl) phenylphosphine oxide (BAPO), to create a UV sensitive reaction.

To select the ratio of polymer to monomer that would be a suitable match for pericardium material, a set of weight to weight ratios of PPF to DEF was tested in thin-film formation, as shown in Table 1. Soluble fraction of the crosslinked composite was measured comparing the dry mass of the film to the dry mass after soluble components were dissolved in acetone for 12 hours, using the following equation:

$$\text{Soluble Fraction \%} = \frac{m_{initial} - m_{final}}{m_{initial}} \times 100$$

Table 1. Compositions of Various Thin Films Tested. Various mass to mass ratios of PPF to DEF were made and then crosslinked into thin films from the same total volume. This change in composition of the uncrosslinked polymer solution can affect the physical properties of the crosslinked result.

| PPF (g) | DEF (g) |
|---------|---------|
| 4 | 1 |
| 3 | 1 |
| 2 | 1 |
| 1 | 1 |
| 1 | 2 |
| 1 | 3 |

Crosslinking. PPF was synthesized according to protocols previously described (MW 2600 Da). The polymer was dissolved within DEF in the following mass ratios of PPF:DEF g:1:2, 1:3. Time and volume dependent cross linking feasibility of these dilutions was determined using curing vessels of various volumes and depths, including a thin sheet formation, in which 100 μl PPF:DEF composites are set between two glass coverslips. All PPF/DEF composites were crosslinked in UVA light (365 nm) with 2 mW/cm². Maximum tensile strength and elastic modulus of the thin sheets were measured. A study of the DEF/PPF sol fraction was performed using the photocrosslinked sheets to determine success of network formation.

Figure 1:
FIG. 1. Thin Film of 2:1 PPF Post-Crosslinking. Thin films of PPF in various weight ratios with DEF were formed from 100 μl of polymer between 2×2 cm glass slides. Polymer crosslinking was initiated with 5 mg/g of BAPO, under UVa light (3.5 mW/cm$^2$) for 90 min. Resulting thin films were 0.25 mm thick and weighed 0.15 grams. The image shows a thin film composed of 2 g PPF to 1 g DEF (2:1).

Mechanical Testing of Polymer Compositions. PPF composite films as previously described were tested on an Instron for mechanical analysis using ASTM D638 to obtain 0.1% yield strength and elastic modulus. Thin-films were formed between two 1.5 cm square glass plates, and resulted in 0.25 mm thick, 0.15 g films (FIG. 1). This geometry is similar to the weight per surface area approximated for coating pericardium, as well as a suitable shape for testing according to ASTM D882. Extension rate was set at 10 mm/min, and extension and corresponding load was recorded at a frequency of 10 Hz. A preload of 5 N was considered. Elastic modulus for each sample was calculated using Matlab to determine the slope of the linear region of the stress-strain curve reported by the Instron. The linear region of the curve was systematically calculated using linear line fit command based on the first 10 data points. The program then continued to add data points in steps of 10 until the $R^2 < 0.97$. The slope of this region was determined to be the modulus of the sample. Strength at 0.1% yield was calculated as the intersection of the stress-strain curve with a line drawn parallel to the linear slope, whose x-axis intercept is shifted 0.01 mm/mm strain.

Sample Preparation.

Throughout this example, PPF reinforced pericardium was compared to GA treated pericardium and untreated pericardium as controls. All pericardium was obtained 2 days after harvest from Innovative Research, Inc. and stored at 4° C. in physiological saline. Experiments were conducted within 2 days of receiving the pericardium, and because the properties of pericardium are thought to vary among individual donors, all samples for each test were taken from the same donor.

Glutaraldehyde treated samples were prepared by immersing small strips of pericardium (2×6 cm) in a 0.625% GA solution for 6 hours at room temperature. Samples were then washed twice and stored in saline at 4° C. PPF reinforced samples were also cut into 2×6 cm strips, and were lightly stretched onto wooden frames to maintain spatial conformation. The tissue was then dehydrated in ethanol dilutions, in order to facilitate the interaction and integration of hydrophobic PPF with pericardium and remove antigenic determinants. Dehydrated pericardium was then coated with a thin and uniform layer of PPF to completely cover the tissue strip. The coated tissue strip was then exposed to UVa light for 90 minutes (3.5 mW/cm²) to crosslink the polymer. After crosslinking, tissue and polymer composite were rehydrated in physiological buffer at room temperature for 2 hours, and then stored in 4° C. Pericardium samples from each group were mechanically tested using the method described previously as controls.

In Vitro Evaluation—Degradation Test An in vitro degradation model was designed to investigate the added strength and resiliency of the PPF reinforcement as compared to untreated pericardium and GA treated pericardium as controls. Pericardium samples were exposed to 0.4 U/mL of collagenase, and shaken at 60 RPM in 37° C. The test was run over a period of 12 days, with mechanical analysis testing performed every 4 days (n=8 per day), as described above. Samples were preserved at various time points for histological analysis.

In Vitro Evaluation—Calcification Test. To compare in vitro calcification between PPF reinforced and GA treated pericardium, samples from these groups were exposed to physiological calcium buffer (2.6 mM calcium/1.6 mM phosphate) at 37° C., for a total period of 45 days. At each time point (5, 12, 21 days), 15 samples from each treatment group were isolated for analysis. For each treatment group, eight of the isolated samples were reserved for mechanical analysis, which was performed as previously described. Two of the samples were preserved for histological study. The final 5 samples were used to quantify calcium deposition. These samples were first triple washed in DI water to remove loosely attached calcium, and then oven dried at 80° C. for 6 hours to measure dry mass. Samples were then hydrolyzed in 2M HCl for 48 hours to dissolve calcium deposits on the tissue. Solutions were then measured for calcium concentration using a colorimetric assay. Calcium concentration at each time point was statistically compared using a student's T test.

In Vivo Evaluation.

Figure 2:
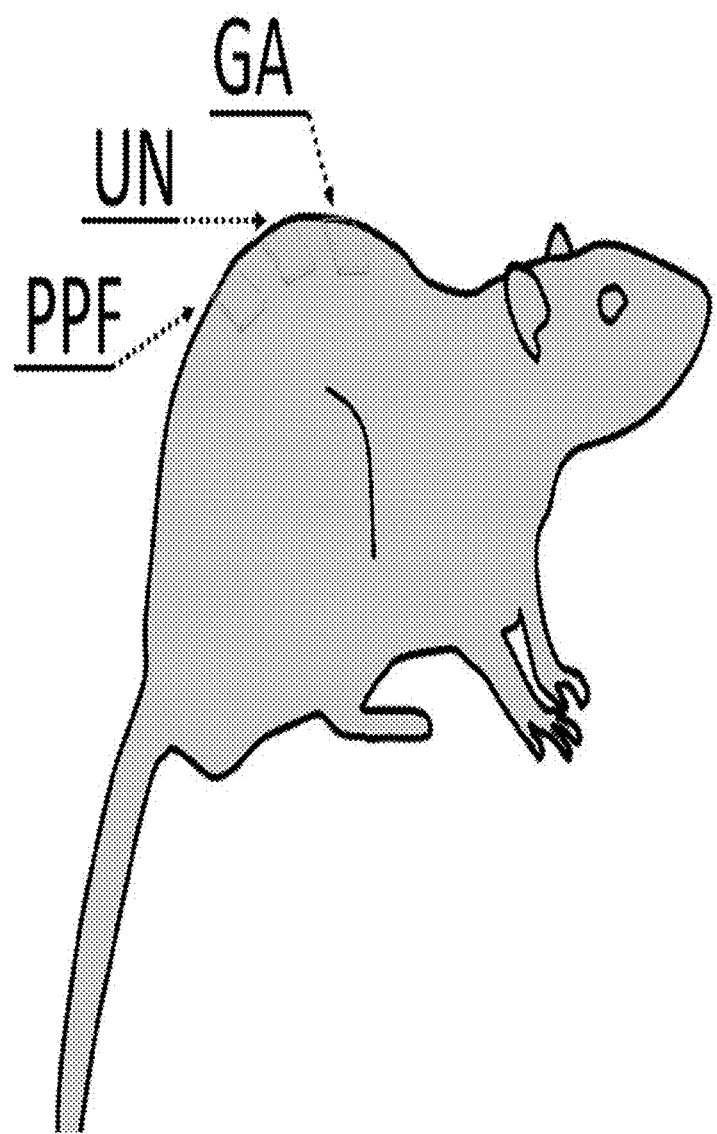
FIG. 2. Schematic of Implantation for Pericardium Patches In Subdermal Rat Model. A small incision was made in the dorsal dermal layer, and a material patch (1×1 cm) from each of the three groups was sutured by the corners to the underlying tissue. Each n=8 animals per time point (n=16 total) received 1 patch from each experimental group.

Calcification rate and material integrity of the hybrid biomaterial were evaluated in a subdermal rat model. The Institutional Animal Care and Use Committee of the University of Maryland approved the study, and all animals were treated in accordance with the "Guide for the Care and Use of Laboratory Animals". The experiment was conducted in n=16 male Sprague Dawley (SD) rats, as determined by a power analysis. As used in known material analysis methods, a small incision is made in the dorsal dermal layer, and a material patch (1×1 cm) from each of the three groups is sutured by the corners to the underlying tissue (FIG. 2). At time points of 3 weeks and 6 weeks, n=8 animals were euthanized and the pericardium patches and surrounding tissue were explanted. Each explanted tissue sample was carefully sliced in half. One half of each sample was preserved in paraformaldehyde (4%) and embedded in paraffin for histological analysis to determine calcium deposition, cellular population and resulting tissue morphology, and inflammatory response.

Inflammatory response in particular was investigated using immunohistochemistry to stain for the presence of the macrophage cell surface antigen F4/80. Slides were incubated with PEROXIDAZED1 (Biocare, Concord, Calif.), an endogenous peroxidase blocker, and BackgroundSNIPER1 (Biocare), a broad spectrum blocking reagent. The samples were then incubated with anti-F4/80 (rabbit polyclonal to F4/80, Abcam ab74384) as the primary antibody, followed by a biotinylated anti-rabbit IgG as the secondary antibody (Vector laboratories). Using a horseradish peroxidase-streptavidin system, followed by a 3,3'-diaminobenxidine tetrahydrochloride chromogen, the presence of the F4/80 molecule was detected. All samples were then counterstained with hematoxylin. Macrophage population was determined through examining 3 standardized images from each of n=5 samples per treatment group. Macrophage fraction was defined as the number of cells determined to have F4/80 staining divided by the total cells counted per image in a blinded study. Data is presented as an average of each of these fractions, and error.

The other half of each sample was dried in a 60° C. oven 18 hours, and then hydrolyzed in 2M HCl for 48 hours. A colorimetric assay was used to determine calcium concentration of each sample.

Statistical Analysis. All quantitative assessments were statistically compared using a one-way ANOVA test, ($p<0.05$), followed by a post hoc Tukey's test, unless otherwise noted.

Figure 3:
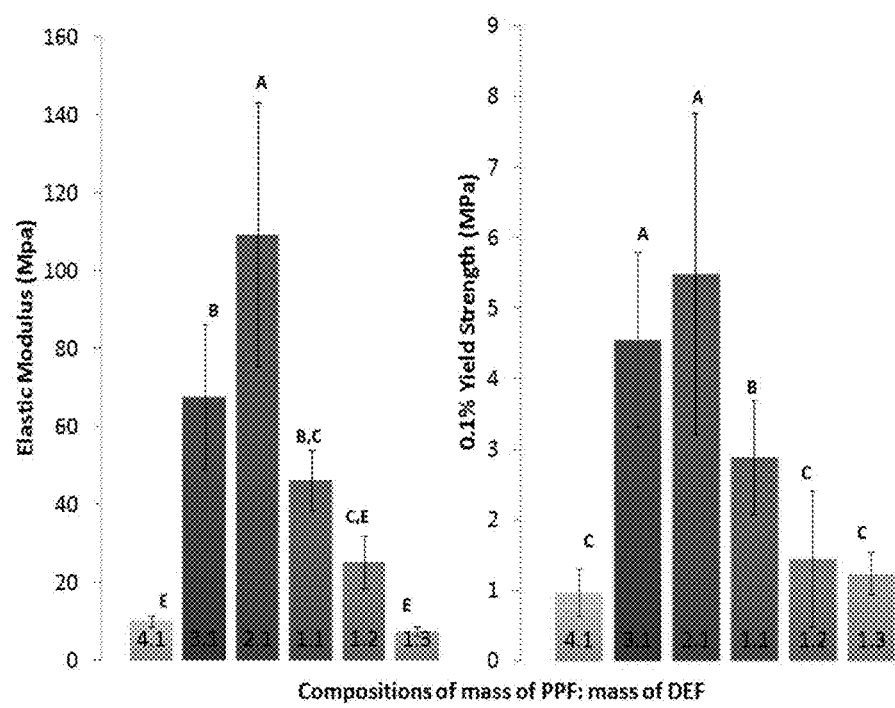
FIG. 3. Elastic modulus and 1% Yield Strength from Thin Films of Various PPF:DEF Composites. Thin films were tested on an INSTRON mechanical tester, and extended at 10 mm/min by a 50 N load cell. N≥7 for all groups, ANOVA statistical test shows significant difference, (p<0.05), and Tukey's Post Hoc results are shown on graph. Groups that do not share a letter are significantly different.
Figure 4:
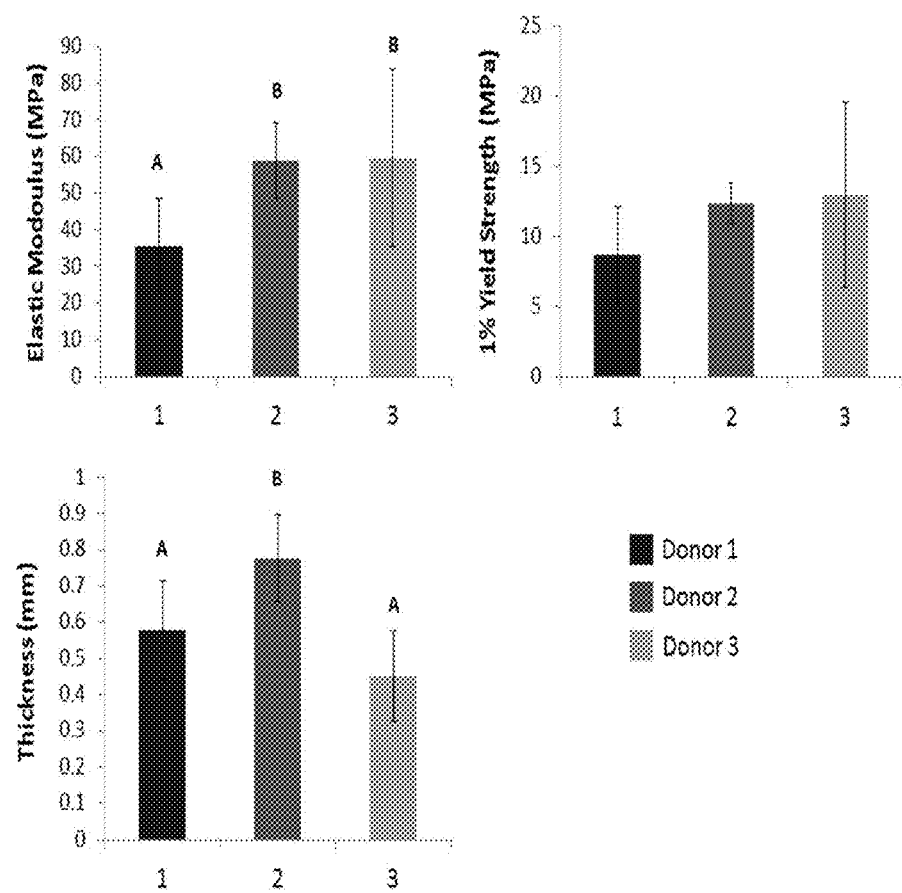
FIG. 4. Untreated Pericardium Physical Properties. The graph displays the characteristic properties collected from pericardium from 3 different donors. All data was collected 2 days after harvest. Samples were cut into 1×5 cm rectangles and stored in PBS until testing. ANOVA statistical tests showed significant difference in the elastic modulus and in the thicknesses (p<0.05), and results from a post hoc Tukey's Test are shown on the graphs. Groups that do not share a letter are significantly different.

Results. We developed a hybrid biomaterial that consists of a polymer reinforcement later painted on the natural biomaterial pericardium. The mechanical characteristics of the polymer directly affect those of the hybrid biomaterial, and were therefore the determining factor in selecting a polymer composite. Following mechanical analysis of the thin-films composed of different formations of PPF:DEF ratios, the 2:1 dilution was selected for future work. The yield strength of this composition (5.48±2.27 MPa) was found to be the greatest, and therefore the closest to the tested values for untreated and GA fixed pericardium (11.32±4.24 and 13.01±4.35 MPa, respectively). A comparison of yield strength and modulus of the thin-films is shown in FIG. 3. The modulus of elasticity and yield stress of pericardium is known to vary between donors based on age and other physiological features, but the values exhibited by the 2:1 films in elasticity measurements are sufficiently high to support the pericardium within the range tested. FIG. 4 displays mechanical analysis data from untreated pericardium from three separate donors, as a reference. The soluble fraction of thin sheets of 2:1 PPF to DEF was calculated as 13.3%±2.7%, (n=9).

Results from the crosslinking feasibility study showed that the physical constraints of decreased volume and depth do not inhibit the formation of a solid network upon photocrosslinking. Furthermore, the significant presence of DEF in the composite increased the flexibility of the thin sheets, as demonstrated in FIG. 1. Preliminary strength measurements showed these sheets to have a maximum strength of 2.17 MPa (±0.89) and an elastic modulus of 23.02 (±6.8). The results from the sol fraction study demonstrate quantitatively that the network has crosslinked significantly over a short time period (10 min), but show an increased sol fraction as DEF content is increased. PPF polymer chains dissolved within DEF are separated by greater distances than in pure PPF, indicating increased DEF concentration could physically inhibit a crosslinked network from forming, as less PPF chains might participate in the crosslinking process.

Figure 5:
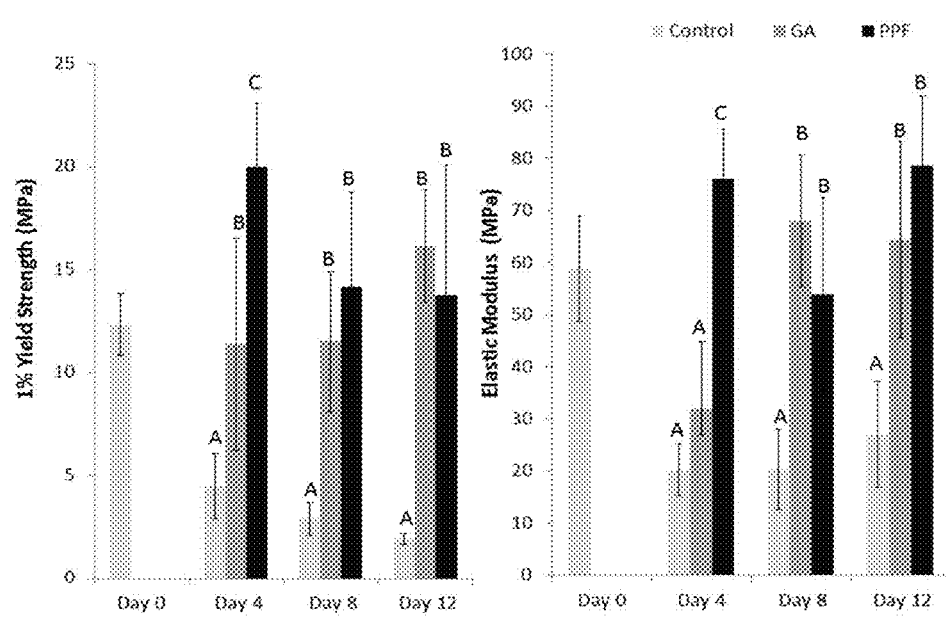
FIG. 5. Mechanical Properties of Pericardium Samples Over Time in In vitro Degradation Model. 1×5 cm rectangle strips of pericardium were either left untreated (control), fixed in 0.625% GA (GA), or reinforced with PPF (PPF). All samples were then degraded in 0.4 U/mL of collagenase, over a period of 12 days. ANOVA statistical test shows significant difference between the treatment methods, compared on the same time point (P<0.05). Results from post hoc Tukey's test are shown on the graph. Groups that share the same letter are not statistically different. The control on Day 0 has no PPF reinforcement or collagenase exposure. Control groups on the following days are exposed to collagenase but not enforced with PPF or GA.
Figure 6:
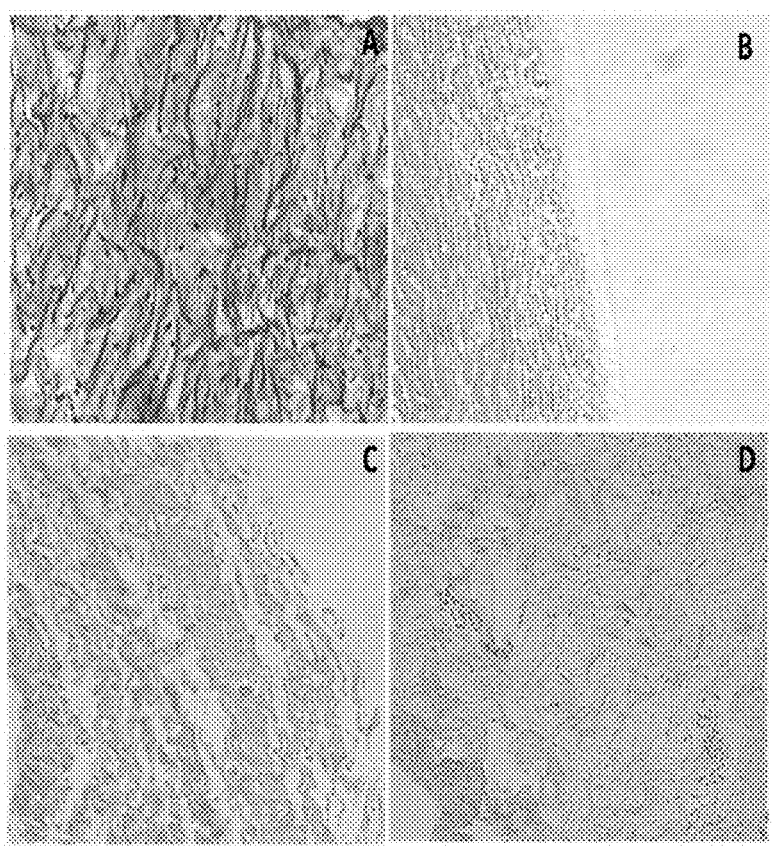
FIG. 6. Histological Analysis of Pericardium Samples from In Vitro Degradation. Samples shown are stained with hematoxylin and eosin to display structure of collagen network. Control pericardium appears to have lost structural integrity after collagenase degradation (D), as did the EtOH dehydrated sample (C), while the sample with PPF reinforcement (B) appears unaltered from the natural pericardium (A).

As mentioned, the 2 PPF:1 DEF composition was selected for further evaluation in the hybrid biomaterial model. After physiological degradation in vitro, mechanical yield strength and elastic modulus of PPF reinforced pericardium are not significantly different than the gold standard GA treated pericardium, ($\alpha=0.05$), (FIG. 5). By day 8, the strength and elasticity of both of these materials still remains above 11.50±3.42 MPa 0.1% yield strength and 54.00±12.67 MPa elastic modulus. These values are comparable to the untreated control on day 0, measured at 12.34±1.49 MPa and 58.80±10.17 MPa, respectively. However, by day 8, the untreated sample has fallen as low as 2.91±0.80 MPa and 20.29±7.76 MPa. These results of reduced or maintained material strength are supported by observations from histological photographs of the pericardium samples, which contrast a highly disordered fresh pericardium fiber network with a more ordered and dense PPF reinforced pericardium sample (FIG. 6).

Figure 7:
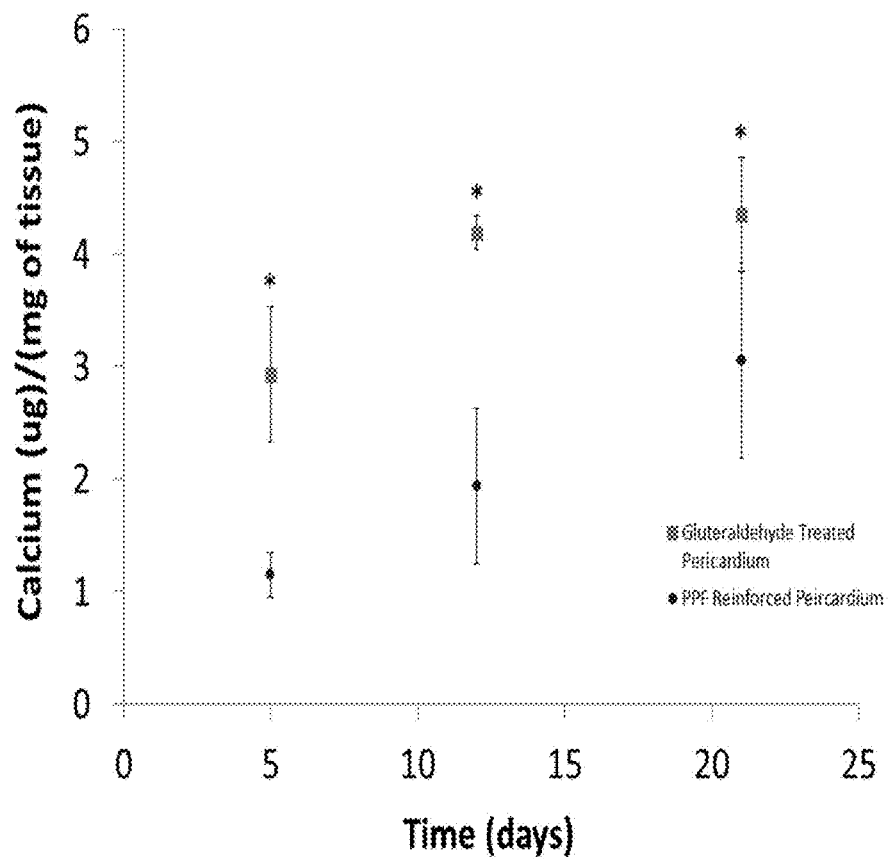
FIG. 7. In vitro Calcification of Pericardium Samples: Quantified Results. Pericardium samples were either left untreated, fixed in 0.625% GA, enforced with PPF. All samples were then stored in a calcium phosphate buffer, and calcium deposition was measured on 0, 5, 12, and 21 days. A students T test shows significant difference between the calcium content for all time points.

In addition to mechanical property retention, calcium deposition was also evaluated in vitro. The time dependent graph in FIG. 7 displays calcium deposition onto GA treated and PPF reinforced tissue from an in vitro calcification model. The level of calcification of GA treated tissue is significantly higher than the level of calcification of PPF enforced tissue at each time point (except day 0), ($p<0.05$). Mechanical data did not show any distinct differences between groups.

Figure 8:
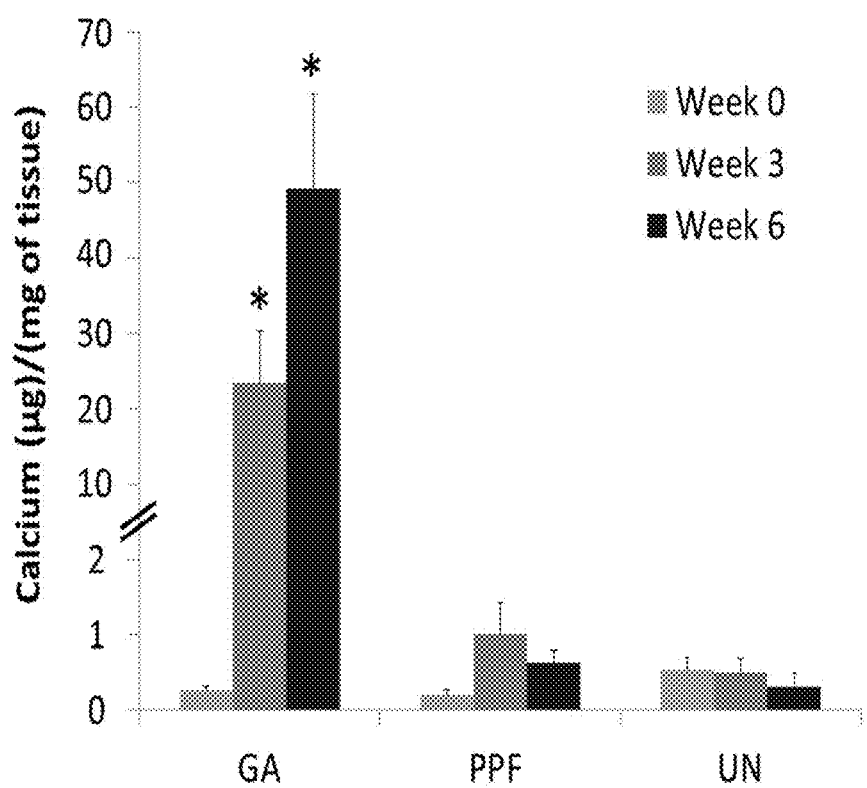
FIG. 8. Calcification of Pericardium Samples from In Vivo Subcutaneous Model: Quantified Results. Calcium content was quantified on samples explanted after 3 and 6 weeks, and compared to non-implanted controls. Calcium content from each sample group was compared for each time point using an ANOVA test (p<0.01).
Figure 9:
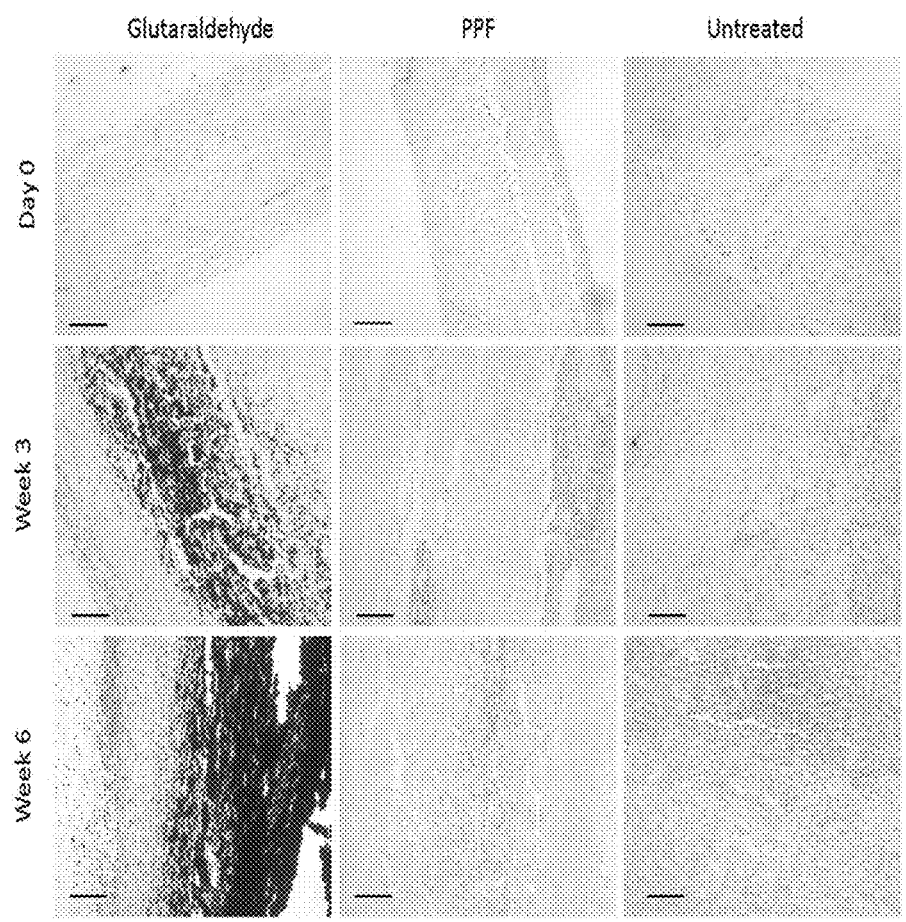
FIG. 9. Calcification of Pericardium Samples from In Vivo Subcutaneous Model: Histological Analysis. Samples explanted at 3 and 6 weeks were fixed and prepared for histological analysis using Von Kossa stains. The dark black region indicates calcium phosphate deposits. This region is seen significantly darker in GA treated samples after 3 and 6 weeks of implantation, and not observed in PPF reinforced or untreated samples.

Calcification was next further evaluated in the in vivo model. Calcification of PPF reinforced pericardium was significantly less than GA treated samples in the quantitative assessment ($p<0.05$) at each time point. The graph in FIG. 8 shows calcium deposition per mass of dried tissue weight compared between the three experimental groups. These results were confirmed by the Von Kossa histological stain (FIG. 9), in which calcium phosphate depositions are observed in GA treated samples on week 3 and 6, but little to no staining is observed on PPF reinforced samples or on untreated samples. The staining in these last two groups appears unchanged from the un-implanted controls (day 0), a result that is confirmed by the maximum variance of ±1 μg of calcium/mg of tissue from the day 0 level over the 6 week period.

Figure 10:
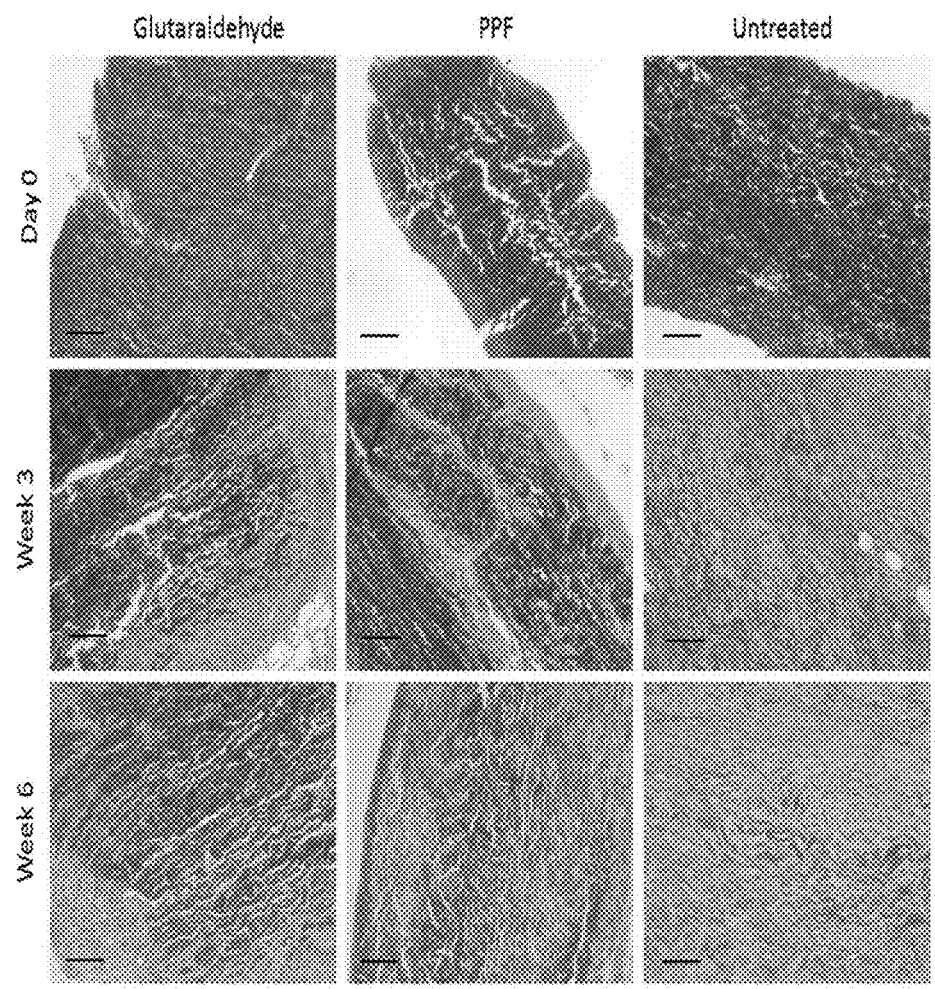
FIG. 10. Histological Analysis of Pericardium Samples from In Vivo Subcutaneous Model. Cellular response to implanted samples was analyzed using Masson's trichrome stain. Blue regions indicate collagen; pink indicates cell bodies. Staining shows local cell populations relative to implanted tissue. Untreated pericardium displays dense cellular regions, suggesting an acute inflammatory response. PPF reinforced and GA treated tissue does not display such a response.

In histological samples stained with Masson's trichrome (FIG. 10), we observe that PPF reinforced tissue remain intact up to 6 weeks, with regions of cellular infiltration. GA treated tissue appears to have limited cell movement into the implanted tissue, but instead has a line of cells near the surface of the implant. Furthermore, GA treated pericardium is observed to exist in a dense network. We further observed untreated tissue was difficult to identify as a distinct material within the surrounding tissue.

Figure 11:
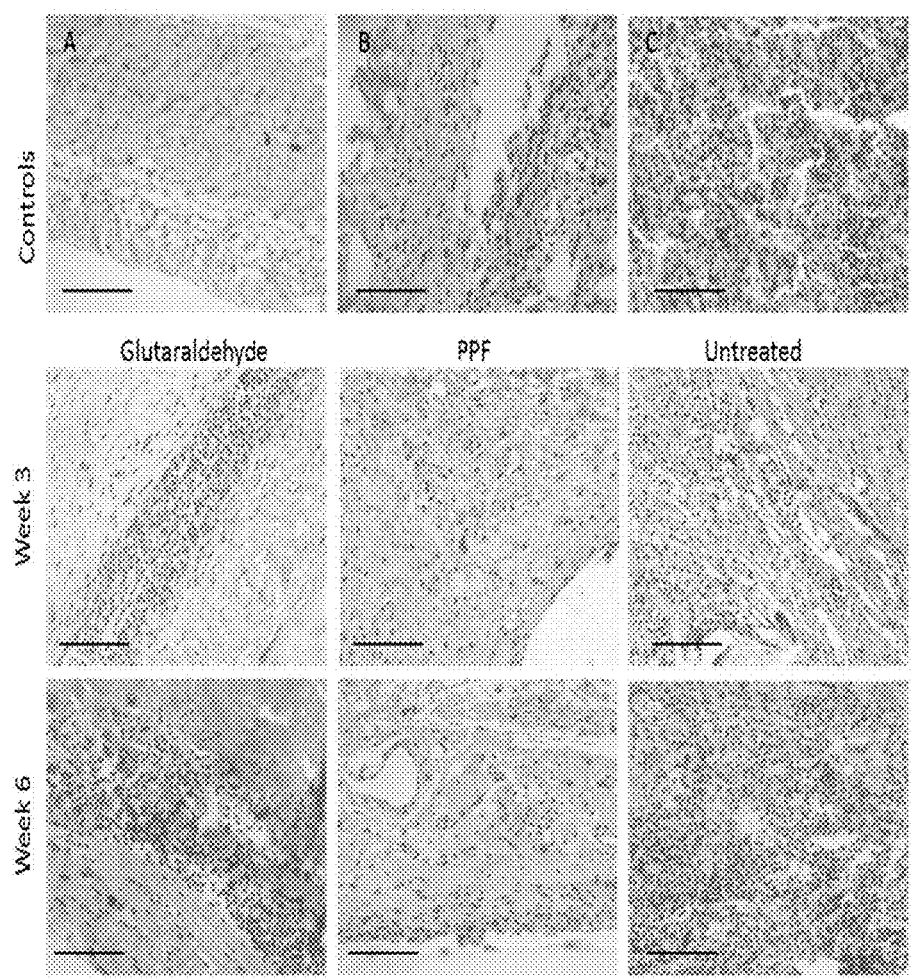
FIG. 11. Immunohistochemical Analysis of Pericardium Samples from In Vivo Subcutaneous Model. Cell populations in the region of the implanted tissues were stained for F4/80, a macrophage surface marker. Staining shows a correlation between dense cell regions and the F4/80 stain, indicating an inflammatory response. A dense line of macrophages is seen near the edge of the GA treated tissue, while in the PPF reinforced and untreated samples, macrophages are seen in smaller regions throughout the sample. On the other hand, there was no significant F4/80 expression in Day 0 samples (A) and samples lacking the primary antigen from week 6 (B). A rat spleen stained by the same procedure is shown in C as a positive control.
Figure 12:
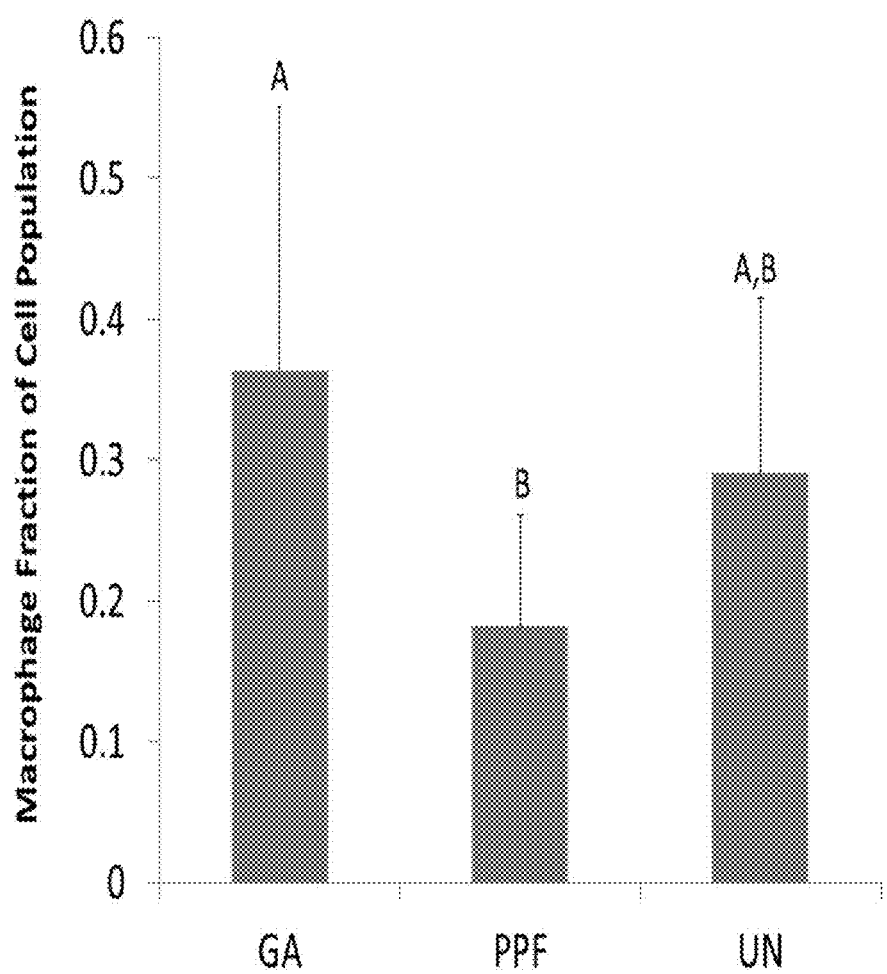
FIG. 12. Macrophage Percent of Cell Population From In Vivo Subcutaneous Model. Macrophage population was investigated by examining 3 standardized images from each of n=5 samples per treatment group. Macrophage fraction was defined as the number of cells determined to have F4/80 staining divided by the total cells counted per image in a blinded study. Data is presented as an average of each of these fractions, and error was calculated as the standard deviation between all images in each group. Population fractions from the GA treated samples and the PPF reinforced samples are significantly different, as determined by a one-way ANOVA test, followed by a post hoc Tukey's test ($p<0.05$).

Using immunohistological staining techniques, it was confirmed that cells expressing the F4/80 surface molecule, a known marker of macrophages, are present at or near the implanted tissue in all treatment groups (FIG. 11). Regions of tissue with dense cell packing also present high amounts of F4/80 stain. In particular, it was observed that the dense cell line seen near the edge of the GA treated tissue has a high presence of F4/80 stain. This is also observed in the other tissue samples, but in small pockets and dispersed throughout the implanted region and neighboring soft tissue. Macrophage fraction of the total cell population in each sample is displayed in FIG. 12. This fraction is greatest in GA treated samples, 36.3±18.7% of the population, and is followed by the untreated samples at 29.0±12.4%, and finally by the PPF reinforced samples at 18.2±8.0%.

Discussion. Utilizing pericardium as a naturally strong and elastic biomaterial offers clear benefits for building cardiovascular devices. In order to utilize pericardium's strengths for a cardiovascular implant, steps need to be taken to preserve the tissue in a foreign body environment. Glutaraldehyde treatment is effective at preventing degradation of the collagen network and preventing immune cell infiltration by crosslinking the collagen fibers. However, this process renders the tissue non-viable, which forces the body to resort to unnatural healing mechanisms to repair inevitable fractures and defects in the tissue. In this process, the natural mechanical properties and hemodynamic capabilities are lost or altered.

To combat the issues caused by GA fixation, strategies that target either therapy with anticalcification agents or biomaterial modifications are among approaches commonly investigated. Biomaterial modifications focus on improving or modifying the GA fixation through altering the reactivity or concentration of the chemical, or using an altogether different chemical process. This last route has included options such as epoxy compounds, carbodiimides, and acyl azides, which all eliminate the use of GA, but still hinge on a chemical crosslink of the tissue. Some of those methods have shown successful results in the laboratory, but have had little translation into clinical practice.

In this example, it was demonstrated that a thin coating of PPF would sufficiently prevent enzymatic degradation of the pericardium tissue, and yet by completely avoiding alteration of the tissue though the use of chemical crosslinker, result in a less calcium deposits.

As demonstrated initially in in vitro degradation, PPF reinforced pericardium did not lose mechanical strength (yield strength or elastic modulus) after collagenase exposure. In fact, the retained elastic modulus and yield strength was not significantly different from the gold standard control (GA treated). This retained strength as demonstrated in mechanical testing and retained physical structure observed in histological images support the superior durability of PPF enforced pericardium when compared to the untreated control in a physiological model. This indicates a thin layer of PPF is successful at protecting pericardium from structural deformation due to enzyme activity. This claim is supported further by results from the sub dermal model. The rapid loss in strength and observed loss in organization of natural pericardium is visually and statistically distinct from the PPF enforced and GA treated pericardium after enzymatic degradation.

Furthermore, the inflammatory response characteristics differ between the PPF reinforced and GA treated cases, as observed with immunohistochemical staining for macrophage presence. In addition to overall lower total macrophage density in PPF reinforced samples; macrophages are homogenously spread throughout the implant. In GA treated samples macrophages are seen in a distinct and dense cell line surrounding the exterior.

More importantly, the calcium deposition in the reinforced pericardium was significantly less than the GA treated samples in both the in vitro and in vivo models. The accumulated calcium on the PPF reinforced samples was in fact so low that is was not significantly higher than either the untreated samples or any of the un-implanted day 0 samples. This result suggests that the calcium deposits are not necessarily related to implanting xenographic tissue, but agrees with the theory that detrimental calcium deposition seen on GA treated implants is related directly to the crosslinking of the tissue. By eliminating the crosslinking component, we have demonstrated an approach that could block calcification of implants before the unnatural healing mechanism starts.

As we have shown, the process of dehydrating and coating the pericardium with the biocompatible polymer PPF interacts with the extracellular matrix in a physical and not chemical or otherwise transformative way. Histological images in FIG. 10 display cellular infiltration from the edges of the samples, indicating that PPF reinforcement leaves the protein matrix suitable for cell viability. These observations can be directly compared to GA treated samples, where little to no cells have migrated into the tissue. This difference suggests that PPF crosslinks into a network on the surface of the pericardium that is mechanically linked in the surface network of proteins, and does not disturb the natural composition. This alternate outcome from the processing of pericardium may explain why the PPF enforced pericardium appears to retain more original structure (FIG. 6), as compared to the dense protein packing in GA treated tissue, as well as why it does not accumulate significant calcium deposits. Overall, the results presented support that the innovative and unprecedented combination of a synthetic polymer with a natural biomaterial may avoid the detrimental end points of GA treated pericardium.

Conclusion. We stablished for the first time a hybrid biomaterial that preserves the natural properties of pericardium and adds support with a biocompatible polymer, while avoiding crosslinking of the tissue. We have shown that the pericardium composite is protected against enzymatic degradation by the paintable application of the polymer, and that the addition of this polymer causes less calcification than the GA treated pericardium. Calcification of cardiovascular devices remains a forefront of concerns. The lower amount of calcium deposition on PPF reinforced pericardium is an important improvement when compared the GA treated calcium accumulation. These results suggest that PPF can be applied to reinforce pericardium instead of glutaraldehyde treated tissue, which is habitually used despite its dangerous and inevitable failure. By eliminating crosslinking with GA, not only would this fate be avoided, but the probability of improved healing and maintenance of the injured or diseased state would be gained. A material with lowered calcification rate would significantly improve the material options and revolutionize expectations for extent of cardiovascular repair.

Example 2

The following in an example of the preparation and characterization of a hybrid biomaterial of the present disclosure.

Biodegradable synthetic materials often serve as the basis for tissue engineering strategies. The biomaterials developed release bioactive molecules while maintaining strength in order to fully utilize the possible capabilities of a synthetic implantable. Directional delivery is important in delivering bioactive materials to a polar environment, such as endothelial tissue, epithelial tissue, or the walls of hollow organs. Using poly(propylene fumarate) (PPF) as a scaffold to encapsulate poly(lactic-co-glycolic acid) (PLGA) microspheres, we achieved tunable and directional release. PPF exhibits properties that support durability in physiological environments. Crosslinked PPF degrades through hydrolysis at a slower rate than PLGA, although both degrade into physiologically occurring compounds. By coating one side of the PPF/PLGA matrix with relatively slow degrading PPF, water contacts the faster degrading PLGA through one side of the matrix, thus creating a single-direction delivery for bioactive factors. Varying ratios of PPF to PLGA were investigated to determine the ideal proportion at which an interconnected network is formed by PLGA within PPF. This network occurred at a mass ratio of 2:1 PPF:PLGA and was confirmed with histological images. Current work assesses a release profile of OVA encapsulated in various formations of PPF/PLGA composites over the degradation time of PLGA. Release is measured with a quantification assay, and directional delivery is confirmed with histology. From this release data, composition can be adjusted to achieve case specific release profiles. This biocompatible structure promotes directional delivery of bioactive materials and is potentially applicable to any implantable or bioactive device.

Designing the microparticles for the PPF reinforced pericardium. Particles made from alginate were considered since alginate is a biocompatible polymer and used as a drug carrier in other tissue engineering applications. Alginate particles, which are hydrogels, lost their shape and composition both when mixed with hydrophobic liquid PPF and during the UV crosslinking process, which does not allow them to exist as drug release tool in the system. We also considered incorporating a concentration of salt as a porogen, which is used with other polymers to create pores by rapidly dissolving out of the cross-linked polymer. However, in the system described, we want the release of loaded factors from the PPF to occur only in the direction of the pericardium, this would mean the salt porogen would flood the pericardium once the construct was rehydrated, creating a super hypertonic environment.

Embedded PLGA Microparticles Directionally Release Bioactive Factors to Pericardium in Hybrid biomaterial. The goal of this work was to develop a directional delivery system for bioactive molecules that can be coupled with a hybrid biomaterial. It was hypothesized that by using PPF as a scaffold to encapsulate PLGA microparticles, a tunable and directional release can be achieved from the intact scaffold. Release will occur as PLGA microparticles degrade hydrolytically into biocompatible molecules, leaving the PPF scaffold unchanged within the release time frame. The system including a layer of PPF with embedded PLGA particles adhered to pericardium is depicted in FIG. 13. In this example, architecture of the composite polymer scaffolds were determined using optical microscopy, degradation was confirmed with gel permeation chromatography (GPC), and ultimately release rates of the model antigen ovalbumin were examined from the composite in vitro. The results of the study suggest that the composite is capable of releasing bioactive molecules over an extended period of time.

Materials and Methods. Microparticles were produced via a double emulsion technique by first dissolving 100 mg of PLGA (Polysciences 50:50, Mw 150,000) in 1 mL of dichloromethane (DCM). An ovalbumin (OVA) stock solution was prepared by dissolving 200 mg of lyophilized OVA in 1 mL of distilled water, and then 200 µL of this stock solution was slowly incorporated into the PLGA/DCM solution with vortexing. The homogeneous PLGA/DCM/OVA solution was then poured into 3 mL of 1% polyvinyl alcohol solution with constant vortexing, followed by alternating vortexing and ultrasonication for approximately 5 minutes. This solution was then poured into 50 mL stirring PVA solution. The solution was left stirring for 4 hours, after which the PVA was removed and the remaining microparticles were washed with deionized water. This process was repeated, and the spheres were then lyophilized.

PPF was synthesized by a two-step process as previously described and initiated using BAPO to create a UV light sensitive reaction. Lyophilized microparticles were then mixed with the PPF solution in a 2:1 (PLGA:PPF) mass ratio. This mixture was then placed between square, glass microscope cover slips and compressed to a uniform thickness of 200 µm. The films were exposed to UV light (3.5 mW/cm$^2$) for 90 minutes in order to initiate photocrosslinking. Ultimately, this results in approximately 50 mg of microparticles per film.

The same formula of PPF and PLGA was also spread over dehydrated pericardium strips, followed by a layer of pure PPF. These tissue strips were crosslinked under UV light, and then washed as described previously. As a control, tissue strips were prepared with only the PPF layer.

To asses PLGA particle degradation, particles were placed in PBS solution (4 mg/5 mL) and incubated at 37 C while shaking for 21 days. At predetermined time points 3 groups of 4 mg of spheres were stopped and lyophilized. After 21 days, all groups were analyzed using GPC to assess molecular weight and number.

Two individual studies were performed in order to measure the rate at which OVA molecules would be released from freestanding microparticles in an aqueous environment, and from microparticles embedded within a PPF thin film. For the microparticles in solution, approximately 25 mg of microparticles were placed in 25 mL of PBS. Each vial was placed on a shaker at 37 C. At each predetermined time interval, 200 µL of solution was removed from the vial and flash frozen for later analysis. 200 µL of PBS was replaced in each vial in order to maintain constant volume. This same procedure was repeated for composite films, where one film is immersed in 25 mL of PBS. After the collection of samples from all time points, the extracted PBS was analyzed using a Bradford protein assay to determine OVA concentration.

Pericardium/PPF/PLGA composites as well as PPF/pericardium strips were individually submerged in 20 mL of PBS and placed on the shaker at 37 C. At time points of 0, 1, 3, 5 and 7 days, a tissue strip was removed from the study and fixed in 4% paraformaldehyde for histological examination. PBS solution was again tested using a Bradford assay for available OVA concentration.

OVA presence in the pericardium tissue resulting from directed release from PPF/PLGA composite was investigated using immunohistochemistry. Slides were incubated with PEROXIDAZED1 (Biocare, Concord, Calif.), an endogenous peroxidase blocker, and BackgroundSNIPER1 (Biocare), a broad spectrum blocking reagent. The samples were then incubated with anti-OVA (rabbit polyclonal to OVA, Abcam ab74384) as the primary antibody, followed by a biotinylated anti-rabbit IgG as the secondary antibody (Vector laboratories). Using an AMCA streptavidin stain, the presence of OVA was detected in the 450 nm range. Images taken at this wavelength were merged with phase contrast microscopy.

Figure 14:
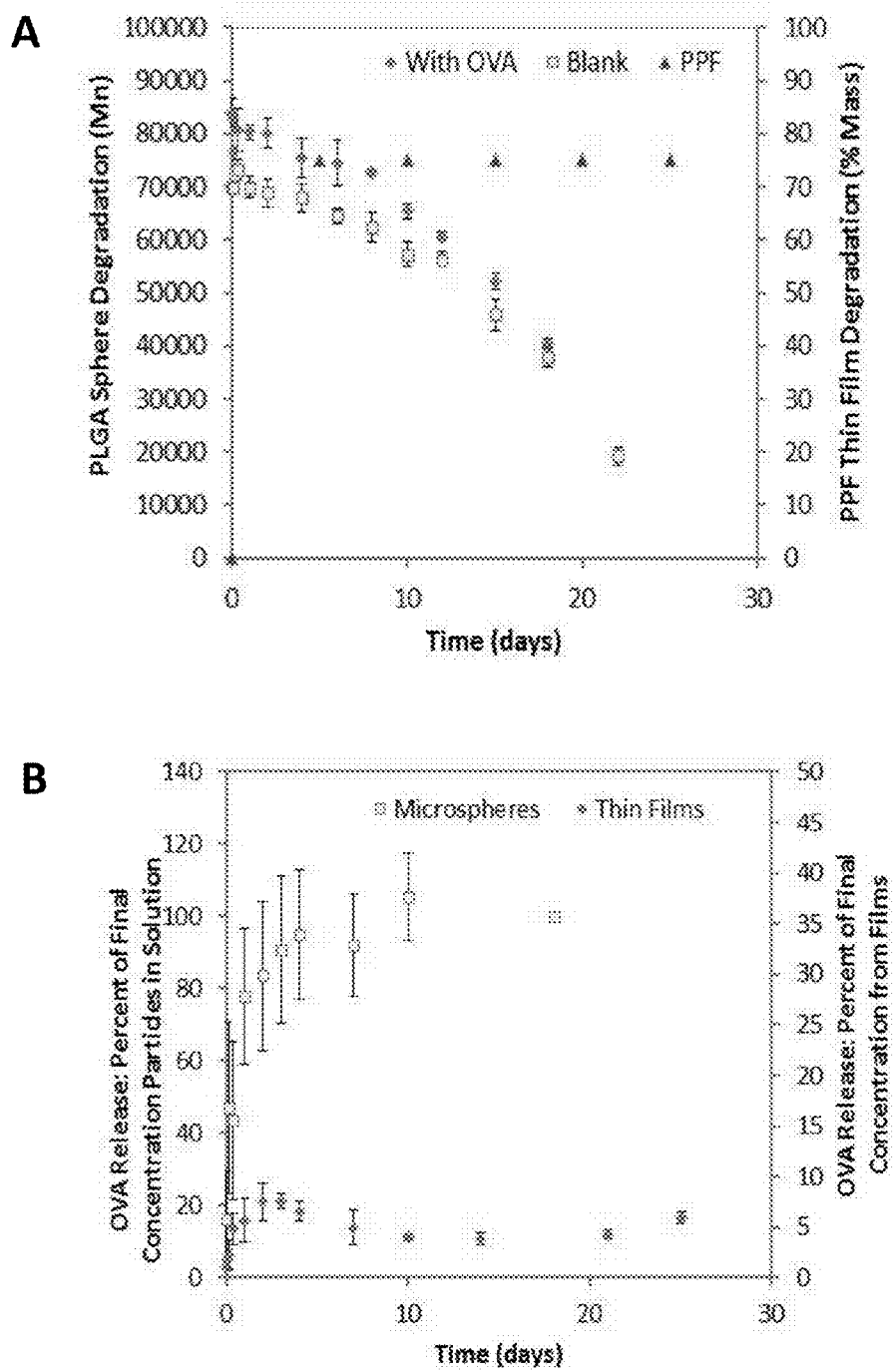

Results and Discussion. The microparticle fabrication resulted in spherical particles between 20-50 µm in diameter, confirmed using light microscopy. The degradation of the PLGA microparticles over 21 days in confirmed in FIG. 14 (A). The starting number average molecular weight of 70,000 is decreased to an average of 20,000 by day 21. The average molecular numbers between OVA loaded and blank microparticles do not differ statistically, as shown by a Student's T test. The degradation of PPF thin films is also shown in FIG. 14 (A), represented by retained mass % over 120 days. The degradation of PLGA is as expected, much faster than PPF, which confirms that the PLGA microparticles will be able to readily degrade into solution and release bioactive molecules while the PPF matrix remains. The lasting PPF construct retains strength and structure in order to hold PLGA microparticles in place while they completely degrade.

The release of OVA from microparticles both free in solution and from within thin films is shown in FIG. 14 (B). The amount of protein is normalized to the mass of PLGA microparticles present. The rate of release from microparticles in solution is comparative rate at which PLGA molecules degrade. In FIG. 14 (B), the release of OVA from microparticles shows an initial and constant release of protein until day 3, at which point the concentration of protein in solution remains constant. This constant concentration is indicative of the maximal protein release from the microparticles. The release from thin films shows an initial release during the first three days, and then the concentration in solution remains constant. The recorded initial release from thin films was recorded at lower concentrations than that of microparticles alone. This difference is expected due to the reduced surface area of microparticles that are exposed to the solution.

The directional release of OVA into pericardium is demonstrated in figure x. A Bradford assay confirms no detectable OVA in solution in the case of either tissue. However, the histological stains confirm its presence in and around the tissue when delivered with the PLGA/PPF layer of the hybrid. As shown in FIG. 15, on Day 0, before little hydrolytic degradation has occurred, the OVA stain (blue) is primarily in the PLGA/PPF layer of the construct. By day 3, some OVA staining is observed in the tissue, and increases by day 5.

By using PPF as a scaffold to encapsulate PLGA microparticles, a tunable and directional release of bioactive molecules can be achieved. Release of OVA will occur as PLGA microparticles degrade hydrolytically into biocompatible molecules. The much slower degrading interconnected PPF network will initially remain, but eventually degrades into biocompatible molecules as well. A benefit of using PPF as a scaffold in order to hold the PLGA microparticles in place is that PPF is a strong and durable material.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

The invention claimed is:

1. A hybrid biomaterial comprising:
   a) a compliant matrix dense tissue substrate;
   b) a first PPF layer comprising cross-linked poly(propylene fumarate) and/or cross-linked copolymer comprising a plurality of cross-linked propylene fumarate moieties; and
   c) a second PPF layer comprising cross-linked poly(propylene fumarate) and/or cross-linked copolymer comprising a plurality of cross-linked propylene fumarate moieties and a plurality of microparticles, a plurality of micropores, or both a plurality of microparticles and a plurality of micropores encapsulated within the cross-linked poly(propylene fumarate) and/or cross-linked copolymer comprising a plurality of cross-linked propylene fumarate moieties;
   wherein,
   the first PPF layer is disposed on at least a portion of a surface of the tissue substrate and the second PPF layer is disposed on at least a portion of a surface of the first PPF layer, or the second PPF layer is disposed on at least a portion of a surface of the tissue substrate and the first PPF layer is disposed on at least a portion of a surface of the second PPF layer.

2. The hybrid biomaterial of claim 1, wherein the cross-linked poly(propylene fumarate) or copolymer comprising a plurality of cross-linked propylene fumarate moieties comprise a plurality of diethylfumarate (DEF) cross-linking moieties, N-vinylpyrollidone cross-linking moieties, or a combination of diethylfumarate cross-linking moieties and N-vinylpyrollidone cross-linking moieties.

3. The hybrid biomaterial of claim 1, wherein the microparticles comprise poly(lactic-co-glycolic acid), poly (ethylene glycol), alginate, gelatin, collagen, poly(ethylene glycol), or a combination thereof.

4. The hybrid biomaterial of claim 1, wherein the microparticles are 50 weight percent to 95 weight percent of the second PPF layer.

5. The hybrid biomaterial of claim 1, wherein the microparticles comprise a bioactive material.

6. The hybrid biomaterial of claim 5, wherein the bioactive material is selected from an antibiotic material, a cytokine, a growth factor, immunosuppressant material, and combinations thereof.

7. The hybrid biomaterial of claim 1, wherein the second PPF layer further comprises a surfactant and the surfactant forms a layer at least partially disposed on a portion of a surface of one or more of the microparticles.

8. The hybrid biomaterial of claim 7, wherein the surfactant is selected from polyvinyl alcohol, vitamin E, 1,2-Dioleoyl-sn-glycero-3-phosphocholine (DOPC), N-(Carbonyl-methoxypolyethyleneglycol 2000)-1,2-distearoyl-sn-glycero-3-phosphoethanolamine (DSPE-PEG), and 1,2-dioleoyl-3-trimethylammonium-propane (DOTAP), and combinations thereof.

9. The hybrid biomaterial of claim 1, wherein the compliant matrix dense tissue substrate has a thickness of 300 micrometers to 1 millimeter and/or an area of 1,000 mm$^2$ to 1,000 cm$^2$.

10. The hybrid biomaterial of claim 1, wherein the first PPF layer and/or second PPF layer has a thickness of 25 micrometers to 1 millimeter and/or an area of 1,000 mm$^2$ to 1,000 cm$^2$.

11. The hybrid biomaterial of claim 1, wherein the poly (propylene fumarate) has a molecular weight of 500 to 4,000 g/mol.

12. A method of making the hybrid biomaterial of claim 1, comprising:
  a) providing an alcohol-dehydrated compliant matrix dense tissue substrate;
  b) coating at least a portion of the substrate with a first mixture comprising poly(propylene fumarate) or copolymer comprising a plurality of propylene fumarate moieties, a cross-linking agent, a photoinitiator, and a plurality of microparticles or a second mixture comprising poly(propylene fumarate) or copolymer comprising a plurality of propylene fumarate moieties, a cross-linking agent, and a photoinititor;
  c) exposing the coated substrate from b) to ultraviolet light such that the poly(propylene fumarate) or copolymer comprising a plurality of propylene fumarate moieties is crosslinked,
  d) if the first mixture is used in b), then coating the substrate from c) with the second mixture,
  e) exposing the coated substrate from d) to ultraviolet light such that the poly(propylene fumarate) or copolymer comprising a plurality of propylene fumarate moieties is crosslinked to provide the hybrid biomaterial,
  f) if the second mixture is used in b), then coating the substrate from c) with the first mixture, and
  g) exposing the coated substrate from d) to ultraviolet light such that the poly(propylene fumarate) or copolymer comprising a plurality of propylene fumarate moieties is crosslinked to provide the hybrid biomaterial.

13. The method of claim 12, further comprising the steps of:
  h) coating at least a portion of the product of g) with a first mixture comprising poly(propylene fumarate) or copolymer comprising a plurality of propylene fumarate moieties, a cross-linking agent, a photoinitiator, and a plurality of microparticles or a second mixture comprising poly(propylene fumarate) or copolymer comprising a plurality of propylene fumarate moieties, a cross-linking agent, and a photoinititor;
  i) exposing the coated substrate from h) to ultraviolet light such that the poly(propylene fumarate) or copolymer comprising a plurality of propylene fumarate moieties is crosslinked,
  j) if the first mixture is used in h), then coating the substrate from i) with the second mixture,
  k) exposing the coated substrate from j) to ultraviolet light such that the poly(propylene fumarate) or copolymer comprising a plurality of propylene fumarate moieties is crosslinked to provide the hybrid biomaterial,
  l) if the second mixture is used in h), then coating the substrate from i) with the first mixture, and
  m) exposing the coated substrate from j) to ultraviolet light such that the poly(propylene fumarate) or copolymer comprising a plurality of propylene fumarate moieties is crosslinked to provide the hybrid biomaterial;
  n) optionally, repeating steps h-n to provide additional layers to the substrate.

14. The method of making the hybrid biomaterial of claim 12, wherein the cross-linking agent is selected from diethylfumarate (DEF), N-vinylpyrrolidone, and combinations thereof.

15. The method of making the hybrid biomaterial of claim 12, further comprising removal of one or more of the microparticles from the hybrid biomaterial.

16. A method for repairing a tissue defect in an individual comprising implanting in a region of the individual a hybrid biomaterial comprising:
  a) a compliant matrix dense tissue substrate;
  b) first PPF layer comprising cross-linked poly(propylene fumarate) and/or cross-linked copolymer comprising a plurality of cross-linked propylene fumarate moieties, and
  c) a second PPF layer comprising cross-linked poly(propylene fumarate) and/or cross-linked copolymer comprising a plurality of cross-linked propylene fumarate moieties and a plurality of microparticles, a plurality of micropores, or both a plurality of microparticles and a plurality of micropores encapsulated within the cross-linked poly(propylene fumarate) and/or cross-linked copolymer comprising a plurality of cross-linked propylene fumarate moieties, wherein the hybrid biomaterial is less immunogenic than a reference material, and
  wherein the first PPF layer is disposed on at least a portion of a surface of the tissue substrate and the second PPF layer is disposed at least a portion of a surface of the first layer, or
  the second PPF layer is disposed on at least a portion of a surface of the tissue substrate and the first PPF layer is disposed on at least a portion of a surface of the second layer.

17. The method for repairing a tissue defect in an individual of claim 16, wherein the microparticles comprise a bioactive material and the bioactive material is released into the individual.

18. The method for repairing a tissue defect in an individual of claim 17, wherein the bioactive material is selected from an antibiotic material, a cytokine, a growth factor, immunosuppressant material, and combinations thereof.

* * * * *